United States Patent
De Groot et al.

(10) Patent No.: US 7,030,996 B2
(45) Date of Patent: *Apr. 18, 2006

(54) MEASUREMENT OF COMPLEX SURFACE SHAPES USING A SPHERICAL WAVEFRONT

(75) Inventors: Peter J De Groot, Middletown, CT (US); Xavier Colonna De Lega, Middletown, CT (US)

(73) Assignee: Zygo Corporation, Middlefield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/806,496

(22) Filed: Mar. 22, 2004

(65) Prior Publication Data

US 2004/0239947 A1 Dec. 2, 2004

Related U.S. Application Data

(63) Continuation of application No. 10/190,353, filed on Jul. 3, 2002, now Pat. No. 6,714,307.

(60) Provisional application No. 60/329,627, filed on Oct. 16, 2001.

(51) Int. Cl.
*G01B 9/02* (2006.01)
(52) U.S. Cl. .................................................. 356/512
(58) Field of Classification Search ............... 356/512, 356/513
See application file for complete search history.

(56) References Cited

U.S. PATENT DOCUMENTS

| | | | |
|---|---|---|---|
| 4,340,306 A | 7/1982 | Balasubramanian | 356/360 |
| 4,387,994 A | 6/1983 | Balasubramanian | 356/513 |
| 4,553,238 A | 11/1985 | Shaw et al. | 372/6 |
| 4,713,822 A | 12/1987 | Lee | 372/69 |
| 4,725,144 A | 2/1988 | Nelson et al. | 356/360 |
| 4,743,117 A | 5/1988 | Kitabayashi et al. | 356/520 |
| 4,872,755 A | 10/1989 | Küchel | 356/360 |
| 4,898,470 A | 2/1990 | Cleaveland | 356/513 |
| 5,048,026 A | 9/1991 | Shaw et al. | 372/6 |
| 5,086,433 A | 2/1992 | Pocholle et al. | 372/72 |
| 5,172,388 A | 12/1992 | Long et al. | 372/70 |
| 5,271,031 A | 12/1993 | Baer | 372/93 |
| 5,285,467 A | 2/1994 | Scheps | 372/69 |
| 5,335,236 A | 8/1994 | Toeppen | 372/25 |
| 5,393,214 A | 2/1995 | Irie et al. | 356/355 |
| 5,398,113 A | 3/1995 | de Groot | 356/360 |
| 5,485,275 A | 1/1996 | Ohtsuka | 356/513 |
| 5,608,166 A | 3/1997 | Monchalin et al. | 73/657 |
| 5,784,164 A | 7/1998 | Deck et al. | 356/359 |

(Continued)

FOREIGN PATENT DOCUMENTS

WO WO 01/27558 4/2001

(Continued)

OTHER PUBLICATIONS

C. Honninger, et al.; *Diode-Pumped Thin-Disk Yb: YAG Regenerative Amplifier*, Applied Physics B, pp. 423-426.

(Continued)

*Primary Examiner*—Hwa (Andrew) Lee
(74) *Attorney, Agent, or Firm*—Fish & Richardson P.C.

(57) ABSTRACT

Conical surfaces (and other complex surface shapes) can be interferometrically characterized using a locally spherical measurement wavefront (e.g., spherical and aspherical wavefronts). In particular, complex surface shapes are measured relative to a measurement point datum. This is achieved by varying the radius of curvature of a virtual surface corresponding to a theoretical test surface that would reflect a measurement wavefront to produce a constant optical path length difference (e.g., zero OPD) between the measurement and reference wavefronts.

29 Claims, 25 Drawing Sheets

U.S. PATENT DOCUMENTS

| | | | | |
|---|---|---|---|---|
| 5,790,303 | A | 8/1998 | Weston et al. | 359/345 |
| 5,872,804 | A | 2/1999 | Kan et al. | 372/93 |
| 5,930,282 | A | 7/1999 | Unternahrer et al. | 372/69 |
| 5,991,035 | A | 11/1999 | Bruning | 356/359 |
| 5,991,315 | A | 11/1999 | Injeyan et al. | 372/11 |
| 6,094,447 | A | 7/2000 | Drake, Jr. | 372/75 |
| 6,134,258 | A | 10/2000 | Tulloch et al. | 372/99 |
| 6,154,279 | A | 11/2000 | Thayer | 356/376 |
| 6,157,663 | A | 12/2000 | Wu et al. | 372/75 |
| 6,167,181 | A | 12/2000 | Fukaishi | 385/123 |
| 6,195,168 | B1 | 2/2001 | De Lega et al. | 356/497 |
| 6,285,704 | B1 | 9/2001 | Kullander-Sjoberg et al. | 372/96 |
| 2001/0028462 | A1 | 10/2001 | Ichihara et al. | 356/512 |
| 2003/0011783 | A1 | 1/2003 | Suzuki et al. | 356/512 |
| 2003/0043385 | A1 | 3/2003 | Kuchel | 356/513 |
| 2005/0134863 | A1* | 6/2005 | De Lega et al. | 356/512 |

FOREIGN PATENT DOCUMENTS

| | | |
|---|---|---|
| WO | WO 01/75395 | 10/2001 |
| WO | WO 02/14845 | 2/2002 |

OTHER PUBLICATIONS

Steven Jackel, et al.; *High-Energy Nd:Dr:GSGG Lasers Based on Phase and Polarization Conjugated Multiple-Pass Amplifiers*; Optical Engineering, vol. 36, No. 7, Jul. 1997, pp. 2031-2036.

K. F. Wall, et al.; *A Ti:Al$_2$O$_3$ Master-Oscillator/Power-Amplifier System*; IEEE Journal of Quantum Electronics, Jun. 1993, No. 6, pp. 1505-1514.

Boppart et al., "Forward-imaging instruments for optical coherence tomography", *Optics Letters*, vol. 22, No. 21, pp. 1618-1620 (Nov. 1, 1997).

Blümel et al., "Absolute interferometric calibration of toric and conical surfaces", *SPIE*, vol. 3134, pp. 370-378 (Jul. 1997).

Brinkman et al., "Testing of rod objects by grazing-indience interferometry experiment", *Applied Optics*, vol. 38, No. 1, pp. 121-125 (Jan. 1, 1999).

Chakmakjian et al., "Simultaneous focus and coherence scanning in interference microscopy", *Technical Digest, International Workshop on Interferometry*, 171 (Riken, Japan, 1996).

Dresel et al., "Three-dimensional sensing of rough surfaces by coherence radar", *Applied Optics*, vol. 31, No. 7, pp. 919-925 (Mar. 1, 1992).

Li et al., "Imaging needle for optical coherence tomography", *Optics Letters*, vol. 25, No. 20, pp. 1520-1522 (Oct. 15, 2000).

Lindner et al., "White-light interferometry via an endoscope", *SPIE*, vol. 4777, pp. 90-101 (Jul. 2002).

Matthys et al., "Panoramic Holointerferometry", *Experimental Mechanics*, vol. 35, No. 1, pp. 83-88 (Mar. 1995).

Schwider, "White-light Fizeau interferometer", *Applied Optics*, vol. 36, No. 7, pp. 1433-1437 (Mar. 1997).

Zhou et al., "Surface profile measurements using a white light Linnik interferometer", *Annual Report Lehrstuhl für Optik, Univ. Elrlangen-Nürnberg* pp. 69 (1996).

* cited by examiner

MEASUREMENT OF COMPLEX SURFACE SHAPES USING A SPHERICAL WAVEFRONT

CLAIM OF PRIORITY

Pursuant to 35 U.S.C. § 120, this application continuation of prior U.S. application Ser. No. 10/190,353, filed Jul. 3, 2002, now U.S. Pat. No. 6,714,307 which claims priority under 35 U.S.C. § 119(e) to Provisional Patent Application No. 60/329,627, filed Oct. 16, 2001. The contents of the prior applications are incorporated herein by reference in their entirety.

TECHNICAL FIELD

This invention relates to optical metrology.

BACKGROUND

A common challenge for manufacturers is precise measurement of surface topography. Examples of manufactured items requiring metrology are engine parts, components for magnetic storage devices, flat-panel displays, molded and textured plastic surfaces, mechanical pump surfaces and seals, and minted coins. In these and other Industrial Markets, there is a significant and growing need for fast, accurate metrology of parts having non-flat prismatic surfaces. These parts include three-dimensional (3D) cones, cylinders, and spheres, often having surfaces as small as 2 mm in diameter and 75 mm deep with 3D form tolerances of as low as 0.5 μm. An important example is fuel system valves, which are fundamental building blocks in engines, pumps and other hydraulic systems. Manufacturing the conical form of these parts within tolerance specifications is a high priority. For instance, the roundness of valve seats is important to valve function as it relates closely to leakage—a valve seat not conforming to specified roundness would likely yield a leaky valve. Additionally, many of these surfaces are deeply recessed within narrow cylindrical holes, making precise metrology even more challenging.

Presently, most measurements on fuel system components are mechanical or tactile (e.g., stylus gages). There is a strong interest in this industry to transition to optical techniques, for example by using interferometry, which can improve throughput, data density and uncertainty compared with mechanical techniques. One key advantage of optics is the "3D" aspect of the surface measurement, as opposed to the linear trace of a stylus gage. However, many industrial surfaces such as interior cones are difficult to measure optically, because of their unusual shape and surface texture, when compared to the usual optical testing samples such as mirrors, prisms and lenses.

SUMMARY

The invention features interferometry methods and systems for measuring complex surface shapes such as internal cones. The most common internal cones requiring precision metrology are one-half of a valve system. The mating part of the valve is generically one of three types: a ball; a mating cone (usually of a slightly more acute angle than the internal cone, and sometimes segmented); and a cylinder (often having a slight taper at the intended contact region with the cone). In each case, "roundness" of the internal cone is important because of the contact surface area between the cone and the mating part. Roundness refers to the deviation of the conical surface from an ideal sphere sitting in the cone at the diameter of contact. This is what gages (in conjunction with other inputs) consistent pressure in the system, accuracy of the duration of the fuel pulse, and leakage (dripping).

The valve contact surface may be thought of as a pie plate with the bottom knocked out. This picture of the contact surface is generally valid for all three types of mating part. For all valve types, the roundness of the contact surface is very important. For cones that mate with other cones, the cone angle and straightness of the contact surface are also very important.

Typically, critical cone surface form characteristics are those that would cause leakage when mated with a ball or similar movable part. Thus, a measurement of most interest to manufacturers of these parts is how the cone surface deviates from the ideal as viewed, e.g., by an imaginary sphere nominally placed at the same position as the actual mating ball of the valve. Therefore, an ideal metrology technique would evaluate the deviation of the conical surface shape (or other complex surface shapes) with respect to a sphere centered on an optical datum point located near the cone axis at a position such that an annular cone-shaped segment of the surface is viewed at near normal incidence from the center of the sphere.

The inventors have recognized that conical surfaces (and other complex surface shapes) can be interferometrically characterized using a locally spherical measurement wavefront (e.g., spherical and aspherical wavefronts). In particular, complex surface shapes are measured relative to a measurement point datum. This is achieved by varying the radius of curvature of a virtual surface corresponding to a theoretical test surface that would reflect a measurement wavefront to produce a constant optical path length difference (e.g., zero OPD) between the measurement and reference wavefronts. This virtual surface is referred to as an optical measurement surface. The radius of curvature of the optical measurement surface can be varied by scanning the OPD in a telecentric portion of the interferometer.

For parts having conical surfaces, the point datum emulates the center of a mating sphere. By scanning the radius of curvature of the optical measurement surface so it tangentially contacts the conical surface, one can measure the gap between the part surface and the optical measurement surface.

Preferably, systems should be configured to satisfy two conditions for optimal measurements using this technique. Firstly, the optical measurement surface should locally match the part surface. In other words, the optical measurement surface should tangentially contact a portion of the part surface. This enables the system to interferometrically measure the part in a direction normal to the part surface. As a result, the lateral calibration of the image pixels is not sensitive, at least to first order, to the 3D nature of the object surface. Likewise, the lateral resolution of the imaging detector does not compromise (at least to first order) the accuracy of the interferometric distance measurement. This is important because the lateral image resolution of an interference microscope is generally 1000 times inferior to the height resolution of the interferometric measurement. Furthermore, the optimal configuration for collecting light reflected by the part surface results when the optical measurement surface tangentially contacts the part surface, which amounts to illuminating and collecting light along the local part normal.

Secondly, the part surface should be in focus with respect to a downstream detector. This optimizes lateral resolution (i.e., in the plane of the part surface) and interference fringe contrast. This condition also reduces measurement sensitivity to the slope of the part surface.

Interferometry systems using this technique can be controlled by e.g., a computer. To measure a portion of a part surface, the computer continuously varies the radius of the optical measurement surface without moving the point datum. As the measurement surface contacts the part surface, the computer records the location of these points of intersection with respect to the optical point datum while acquiring images of corresponding interference patterns via a detector. Using an algorithm, the computer reconstructs and analyzes the part surface.

In general, in a first aspect, the invention features an interferometry method. The method includes directing a measurement wavefront to reflect from a measurement surface and a reference wavefront to reflect from a reference surface, where the measurement and reference wavefronts are derived from a common light source, and directing the reflected measurement and reference wavefronts to overlap with one another and form an interference pattern. Paths for the measurement and reference wavefronts define an optical measurement surface corresponding to a theoretical test surface that would reflect the measurement wavefront to produce a constant optical path length difference between the measurement and reference wavefronts. The method also includes varying the radius of curvature of a locally spherical portion of the optical measurement surface to contact a conical portion of the measurement surface, and detecting the interference pattern as a function of the radius of curvature.

In another aspect, the invention features an interferometry method that includes directing a measurement wavefront to reflect from a measurement surface and a reference wavefront to reflect from a reference surface, where the measurement and reference wavefronts are derived from a common light source having a coherence length. The method includes directing the reflected measurement and reference wavefronts to overlap with one another and form an interference pattern. Paths for the measurement and reference wavefronts define an optical measurement surface corresponding to a theoretical test surface that would reflect the measurement wavefront to produce a constant optical path length difference between the measurement and reference wavefronts. The method further includes varying the radius of curvature of a locally spherical portion of the optical measurement surface to contact the measurement surface, and detecting the interference pattern as a function of the radius of curvature, wherein the radius of curvature is varied over a distance greater than the coherence length of the light source.

In a further aspect, the invention features an interferometry method that includes directing a measurement wavefront to reflect from a measurement surface and a reference wavefront to reflect from a reference surface, where the measurement and reference wavefronts being are from a common light source, and directing the reflected measurement and reference wavefronts to overlap with one another and form an interference pattern. Paths for the measurement and reference wavefronts define an optical measurement surface corresponding to a theoretical test surface that would reflect the measurement wavefront to produce a constant optical path length difference between the measurement and reference wavefronts. The method also includes varying the radius of curvature of a locally spherical portion of the optical measurement surface to contact the measurement surface, detecting the interference pattern as a function of the radius of curvature, and generating a radial height profile. The radial height profile corresponds to the distance between the measurement surface and the optical measurement surface at a particular radius of curvature along a normal to the optical measurement surface at the particular radius of curvature.

In yet a further aspect, the invention features a method for calibrating an interferometric system using a calibration artifact having a known shape. The method includes directing a measurement wavefront to reflect from the calibration artifact and a reference wavefront to reflect from a reference surface, where the measurement and reference wavefronts are derived from a common light source, and directing the reflected measurement and reference wavefronts to overlap with one another and form an interference pattern. Paths for the measurement and reference wavefronts define an optical measurement surface corresponding to a theoretical test surface that would reflect the measurement wavefront to produce a constant optical path length difference between the measurement and reference wavefronts. The method further includes varying the radius of curvature of a locally spherical portion of the optical measurement surface to contact the calibration artifact, detecting the interference pattern as a function of the radius of curvature, and generating a radial height profile. The radial height profile corresponds to the distance between the calibration artifact and the optical measurement surface at a particular radius of curvature along a normal to the optical measurement surface at the particular radius of curvature. The interferometry system is calibrated based on the radial height profile.

In another aspect, the invention features an interferometry system. The interferometry system include a light source having a coherence length and an interferometer positioned to derive measurement and reference wavefronts from the light source. During operation the interferometer directs the measurement wavefront to reflect from a measurement surface and the reference wavefront to reflect from a reference surface, and further directs reflected measurement and reflected reference wavefronts to overlap with one another and to form an interference pattern, wherein paths for the measurement and reference wavefronts define an optical measurement surface corresponding to a theoretical test surface that would reflect the measurement wavefront to produce a constant optical path length difference between the measurement and reference wavefronts. The system also includes a translation stage coupled to the interferometer to vary the radius of curvature of a locally spherical portion of the optical measurement surface to contact the measurement surface. The translation stage varies the radius of curvature over a distance greater than the coherence length of the light source. The system further includes a detector (e.g., a CCD detector) positioned to detect the interference pattern as a function of the radius of curvature.

The aforementioned interferometry methods and system can include one or more of the following features.

The constant optical path length difference can be a zero optical path length difference.

The radius of curvature can be varied over a distance greater than the coherence length of the light source. Alternatively, the radius of curvature can be varied over a distance less than the coherence length of the light source. The radius of curvature can be varied according to a phase-shifting algorithm.

The optical measurement surface can be a spherical or aspherical optical measurement surface. The radius of curvature can be varied relative to a fixed measurement datum point.

The measurement surface can include a conical surface.

Directing the measurement wavefront to reflect from the measurement object can include focusing the measurement wavefront towards a measurement datum point, which can be positioned prior to the measurement surface. Similarly, Directing the reference wavefront to reflect from the reference surface can include focusing the reference wavefront towards a reference focal point, which can be positioned prior to the reference surface. Moreover, the reference wavefront can be reflected from a curved portion of the reference surface, and can be reflected back to the reference focal point. Varying the radius of curvature of the optical measurement surface can include translating the reference focal point, which can include translating reference optics used to focus the reference wavefront towards the reference focal point. Varying the radius of curvature can further include translating the curved portion of the reference surface simultaneously with translating the reference optics.

Alternatively, or additionally, varying the radius of curvature of the optical measurement surface can include translating the measurement datum point. Translating the measurement datum point can include translating measurement optics used to focus the measurement wavefront towards the measurement datum point. The measurement surface can be translated simultaneous to translating the measurement optics.

Directing the reflected measurement and reference wavefronts to overlap with one another and form the interference pattern can include imaging the reflected measurement and reference wavefronts to overlap with one another on a planar image plane. The interference patterns can be detected at the planar image plane. A portion of the optical measurement surface tangential to the measurement surface can also be imaged to the planar image plane. Imaging can include positioning a collimating optic at the measurement datum point. Alternatively, or additionally, imaging can include positioning a stop about the measurement datum point.

The methods and/or systems can map the interference image to a portion of the measurement surface, wherein a distance between a point in the interference image and a common reference point in the image is related to a chief ray angle at the optical measurement surface. The common reference point in the image can correspond to an optical axis of an imaging system used to overlap the reflected measurement and reference wavefronts.

The methods and/or systems can generate a radial height profile based on the interference patterns, wherein the radial height profile corresponds to the distance between the measurement surface and the optical measurement surface at a particular radius of curvature along a normal to the optical measurement surface at the particular radius of curvature. The methods and/or systems can reconstruct the measurement surface in Cartesian coordinates based on the radial height profile, and can determine a deviation of the measurement surface from an ideal conical surface.

The optical measurement surface can tangentially contact a portion of the measurement surface while the radius of curvature is varied.

The lateral position of the measurement surface can be translated relative to an optical axis of an imaging system used to overlap the reflected measurement and reference wavefronts.

The measurement surface can be imaged onto an image plane. The reference surface can also be imaged onto the image plane, and overlapping reflected measurement and reference wavefronts can be detected at the image plane, e.g., using an electro-optic detector. The detected interference patterns can be recorded for, e.g., offline analysis. These recorded interference patterns can be analyzed using a computer processor.

Analysis of the interference patterns can include can include reconstructing the measurement surface in Cartesian coordinates based on a radial height profile. The radial height profile and/or analysis can be determined/performed using a computer processor. Analysis can further include determining a deviation of the measurement surface from an ideal conical surface, e.g., at a particular cone diameter. The deviation can be determined in a direction perpendicular to the ideal conical surface. Parameters such as a cone angle and a cone axis can be determined from the ideal conical surface.

Calibration artifacts can include a spherical surface, e.g., a spherical surface. Calibrating interferometry systems can include reconstructing a calibration artifact in Cartesian coordinates based on a radial height profile. Calibrating can further include determining the position of the calibration artifact with respect to a measurement point datum based on the reconstructed calibration artifact. Calibrating can also include moving the optical measurement surface relative to the calibration artifact based on the position of the calibration artifact.

In interferometry systems, the translation stage can vary the optical path length difference by translating the reference surface.

Interferometers can include reference optics (e.g., a reference lens that that focuses the reference wavefront towards a reference focal point) positioned to direct the reference wavefront to the reference surface and to direct the reflected reference wavefront to the detector. The translation stage can vary the optical path length difference by translating the reference surface and the reference optics.

The reference surface can be a planar surface or a curved surface (e.g., spherical surface).

Interferometry systems can include an object mount for positioning the measurement surface in the interferometer. The object mount can position the measurement surface (e.g., a conical measurement surface) in the interferometer so that when the radius of curvature is varied the measurement optical surface contacts at least a portion of the measurement surface.

Interferometers can include measurement optics positioned to shape the measurement wavefront into a locally spherical measurement wavefront and to direct the reflected measurement wavefront to the detector. The translation stage can vary the optical path length difference by translating the object mount and measurement optics. The measurement optics can include an objective lens that focuses the measurement wavefront toward a measurement point datum. The measurement point datum can be located on an optical axis of the measurement optics. Alternatively, or additionally, the measurement optics can include an aperture stop and the measurement point datum is located at the aperture stop. The measurement optics can also include a collimating optic and the measurement point datum can be located at the collimating optic. The collimating optic can increase the numerical aperture of the measurement optics.

The reference surface can be located between the measurement optics and the measurement surface.

The interferometer can include imaging optics that image a portion of the measurement surface to an image plane. The imaging optics can also image the reference surface to the image plane. The translation stage can vary the radius of curvature so that the optical measurement surface contacts (e.g., tangentially contacts) the portion of the measurement surface imaged to the image plane. The detector can be positioned at image plane. Translating the translation stage can cause the magnification of the image to change.

The interferometer can include a telecentric portion. The translation stage can vary the radius of curvature of the optical measurement surface by varying the optical path length difference between the measurement and reference wavefronts in the telecentric portion.

Any of the interferometry systems can include a controller in communication with the detector and the translation stage. During operation, the controller can cause the translation stage to vary the radius of curvature and can record interference signals from the detector.

The interferometer can be, e.g., a Twyman-Green interferometer or a Fizeau interferometer.

The light source can be a broadband, narrowband, or monochromatic light source. The light source can be a point source (e.g., a super-luminescent diode) or an extended source.

Embodiments of the invention have many advantages. For example, one can measure both rough and smooth surfaces. Furthermore, one can measure conical surfaces with different cone angles. In some embodiments, many of the optical components are common to both the measurement and reference beams, which reduce the influence of imperfections in the optics to measurements. More generally, embodiments provide three-dimensional information about a conical measurement surface and/or other complex surfaces.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the systems, methods, and examples are illustrative only and not intended to be limiting.

Other features and advantages of the invention will be apparent from the following detailed description, and from the claims.

DESCRIPTION OF DRAWINGS

Like reference symbols in the various drawings indicate like elements.

DETAILED DESCRIPTION

The inventive apparatus therefore performs an all-optical evaluation of the deviation of the conical and other complex surface shapes with respect to a sphere centered on an optical point datum located near to the cone axis at a position such that an annular cone-shaped segment of the surface is viewed at near normal incidence from the center of the sphere.

Figure 1:
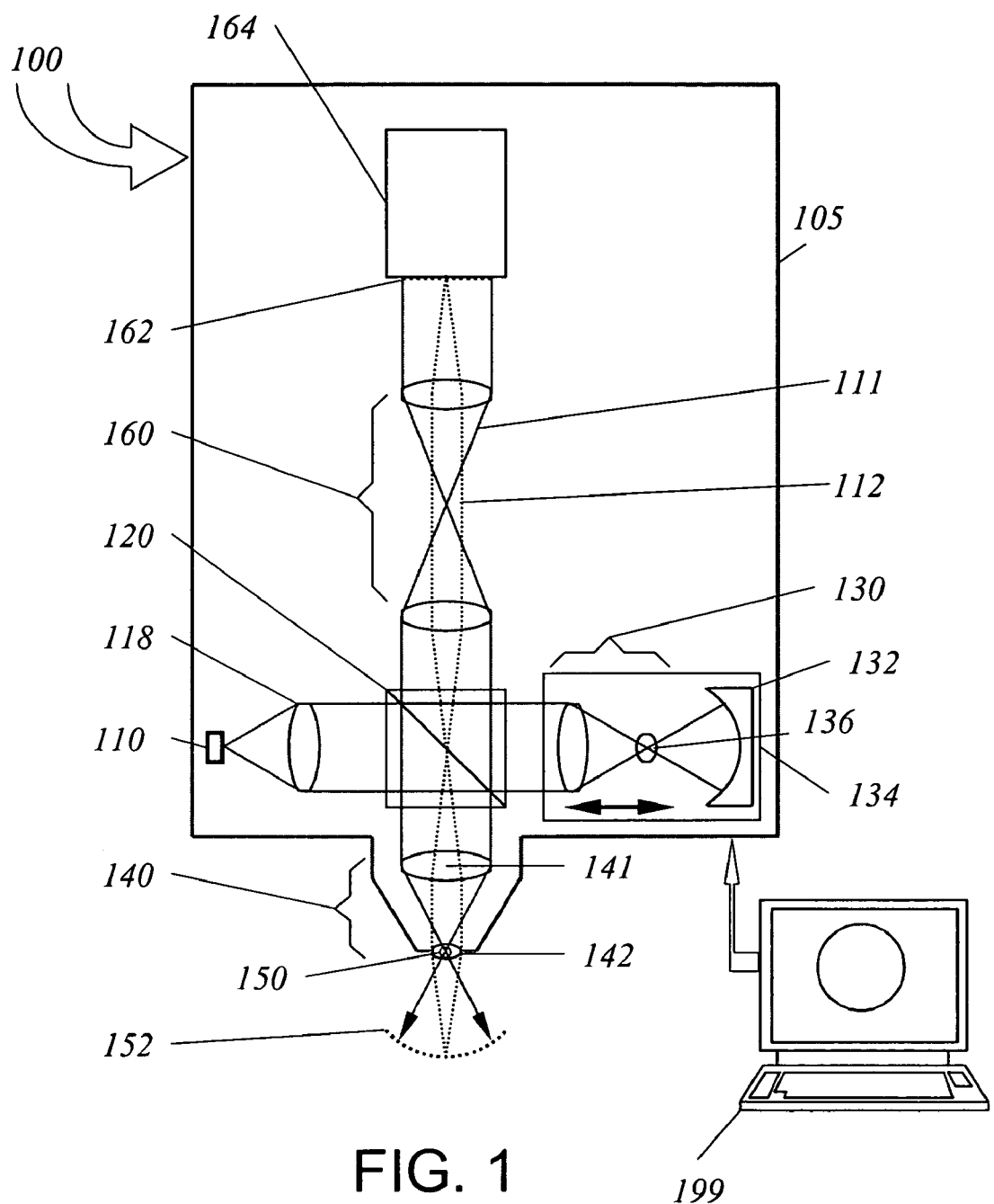
FIG. 1 is a schematic diagram of a sensor based on a Linnik interferometer with a scanning reference assembly.

FIG. 1 shows an embodiment of an optical sensor 100 housed in an enclosure 105. Sensor 100 includes an interferometer, which consists of a beam splitter 120, measurement optics 140 and reference optics 130. A light source 110 (e.g., a low-coherence source such as a halogen bulb, light emitting diode (LED), super-luminescent diode (SLD)) illuminates reference optics 130 and measurement optics 140 with respective measurement and reference wavefronts via an illuminator lens 118 and beam splitter 120. Measurement and reference wavefronts reflect from a measurement surface (not shown) and a reference mirror 132. At an image plane, imaging optics 160 image reflected measurement and reference wavefronts to a flat-field image plane 162. A CCD camera 164 detects the imaged wavefronts at flat-field image plane 162.

The interferometer is similar to a Linnik interferometer, in which reference optics 130 essentially duplicate the measurement optics 140 to compensate for chromatic dispersion and optical aberrations. Measurement optics 140 are specifically designed to generate a locally spherical measurement wavefront in object space, centered on a measurement datum point 150, such that a chief ray 111 passes through measurement datum point 150. In this case, datum point 150 is also the pupil of measurement optics 140. Measurement optics 140 includes an objective lens 141 and a collimating lens 142. Collimating lens 142 focuses the marginal rays while increasing the numerical aperture of measurement optics 140, which through imaging optics 160 image marginal ray 112 to flat-field image plane 162. While measurement optics 140 include two lenses, more generally measurement optics can include fewer (e.g., a single lens) or more optical components. Similarly, while reference optics 130 includes two lenses; in other implementations reference optics can include fewer or more optical components. Furthermore, in other embodiments the reference optics are omitted entirely, and curved reference mirror 132 is replaced with a planar reference mirror. However, in this latter embodiment, chromatic dispersion and optical aberrations in the measurement optics may not be compensated. In this case, additional optical components can be included between beamsplitter 120 and the planar reference mirror to compensate for measurement optics 140. Such optical components can include, e.g., one or more properly chosen parallel glass plate(s), or an afocal telecentric system with dispersion matching the dispersion introduced by measurement optics 140.

Reference optics 130 focus the reference wavefront to a reference focal point 136. Thereafter, the reference wavefront contacts curved reference mirror 132, whose curvature matches the expanding reference wavefront and reflects the reference wavefront back towards beam splitter 120. Reference optics 130 and reference mirror 132 are mounted on a translation stage 134, which translates reference focal point 136 relative to beamsplitter 120. Translating reference focal point 136 varies the optical path difference (OPD) between the measurement and reference wavefronts. By translating reference optics 130 with reference mirror 132, translation stage 134 varies the OPD in a telecentric portion of the interferometer.

Paths for the measurement and reference wavefronts define an optical measurement surface 152 corresponding to a theoretical test surface that would reflect the measurement wavefront to produce a constant OPD between the measurement and reference wavefronts. In the present embodiment, reference mirror 132 is arranged so optical measurement surface 152 corresponds the surface of zero OPD between the measurement and reference wavefronts. Measurement surface 152 therefore represents the instantaneous locus of zero OPD points in space, with all points in focus at a nominal radius of curvature, at least substantially over a limited range of ray angles. Optical measurement surface 152 coincides with a focal surface of measurement optics 140 and imaging optics 160. Accordingly, a measurement surface coincident with optical measurement surface 152 is imaged to flat-field image plane 162 and also produces reflected measurement wavefronts that have a zero OPD with reference wavefronts reflected from reference mirror 132.

Sensor 100, under control of a computer 199, accepts electronic intensity data from camera 164 while varying the OPD by scanning translation stage 134. Adjusting the reference beam path length changes the radius of curvature for measurement surface 152, effectively scanning a measurement area with respect to measurement point datum 150, like an inflating balloon, while datum point 150 remains substantially fixed.

Figure 2A:
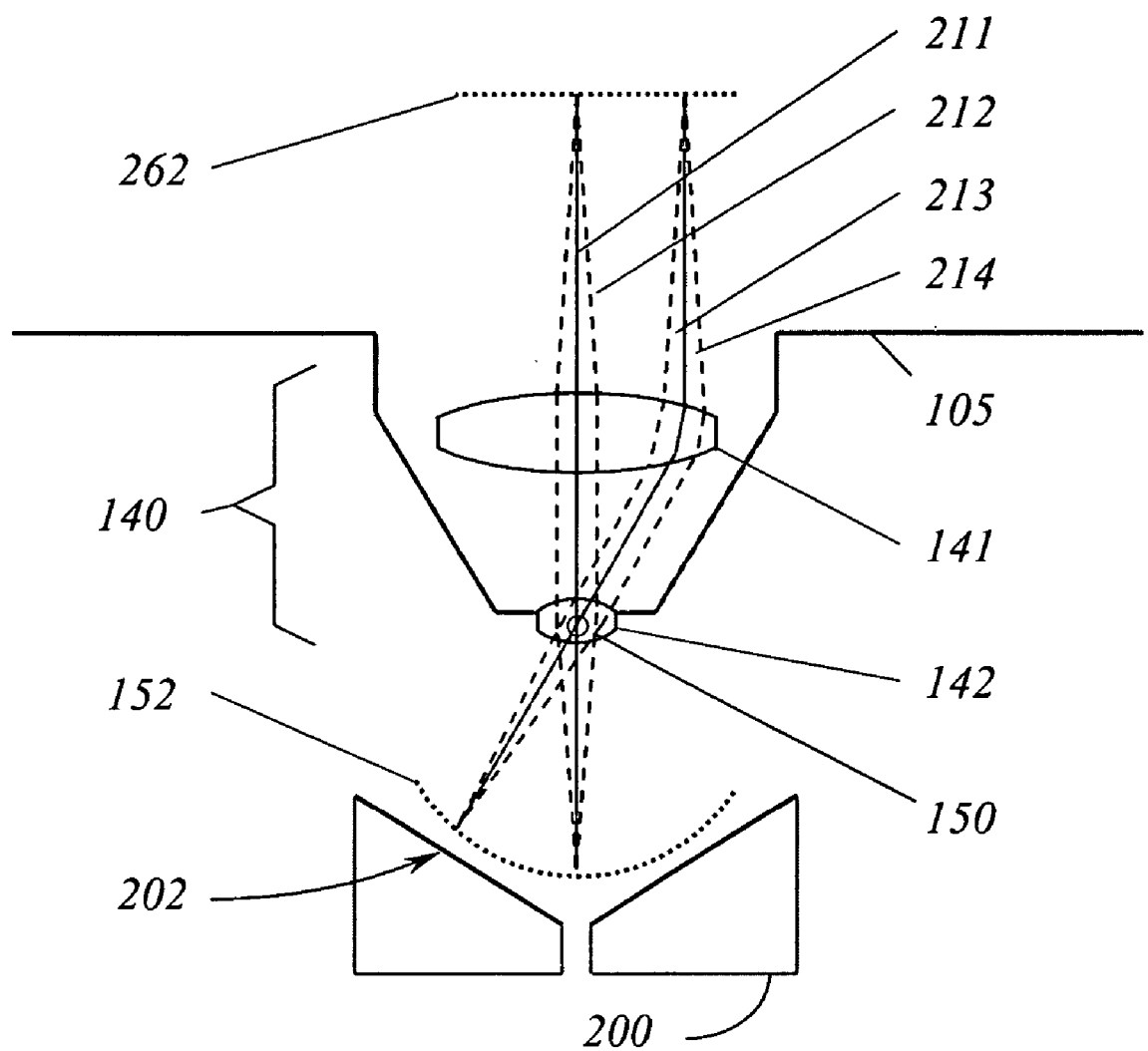
FIG. 2(a) shows detail of the measurement optics of the sensor shown in FIG. 1.

FIG. 2(a) shows measurement optics 140 in greater detail, arranged so as to measure a conical part surface 202 for a part 200, shown here in cross section. Note that chief rays 211 and 213 both pass through measurement datum point 150 near the center of collimating lens 142. Collimating lens 152 focuses marginal rays 212 and 214 from reflected from measurement surface 152 back to a substantially flat intermediate real image 262.

Figure 2B:
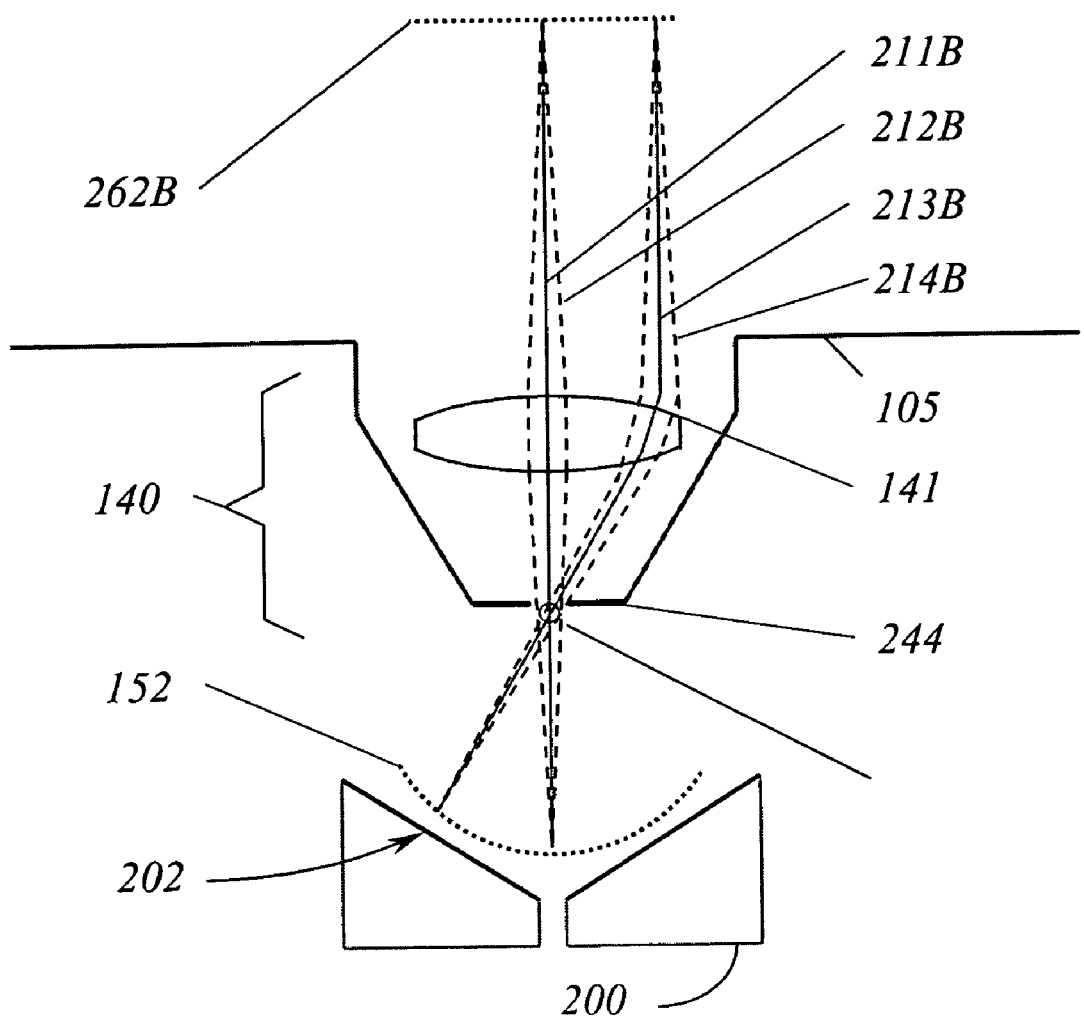
FIG. 2(b) shows alternative measurement optics for the sensor shown in FIG. 1.

FIG. 2(b) shows an alternative arrangement for measurement optics 140 without a collimating lens positioned at measurement datum point 150. Here, measurement optics 140 includes objective lens 141, which focuses chief rays 211B and 213B to measurement point datum 150—in other words, measurement datum point 150 is located at the focal plane of objective lens 141. An aperture stop 244 is positioned at measurement datum point 150. Objective lens 141 focuses marginal rays 212B and 214B reflected from measurement surface 202 back to substantially flat intermediate real image 262B.

Figure 3:
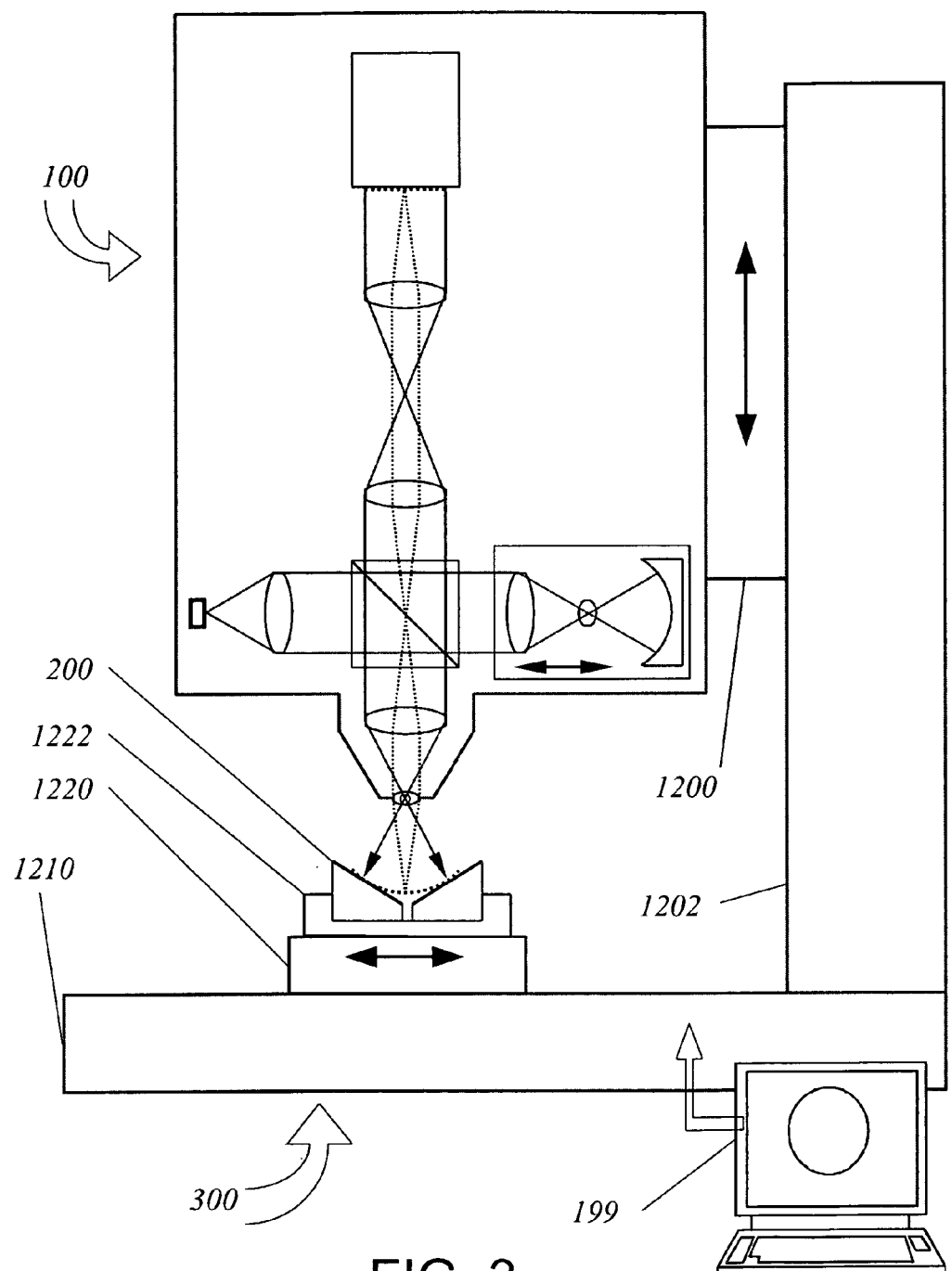
FIG. 3 is a schematic diagram of an interferometry system including the sensor of FIG. 1 and x,y,z staging.

Various system configurations are possible for mounting and positioning sensor 100. In FIG. 3, for example, interferometry system 300 includes sensor 100 mounted to a z stage 1200 (i.e., a vertical translation stage) on a pillar 1202 affixed to a base 1210. An x, y stage 1220, also affixed to base 1210, aligns a part fixture 1222 positioning part 200 with respect to sensor 100. Optionally, base 1210 includes tip-tilt staging (not shown) for adjusting the angular orientation of part 200 with respect to measurement optics 130. Computer 199 controls the entire system, including staging.

Figure 4:
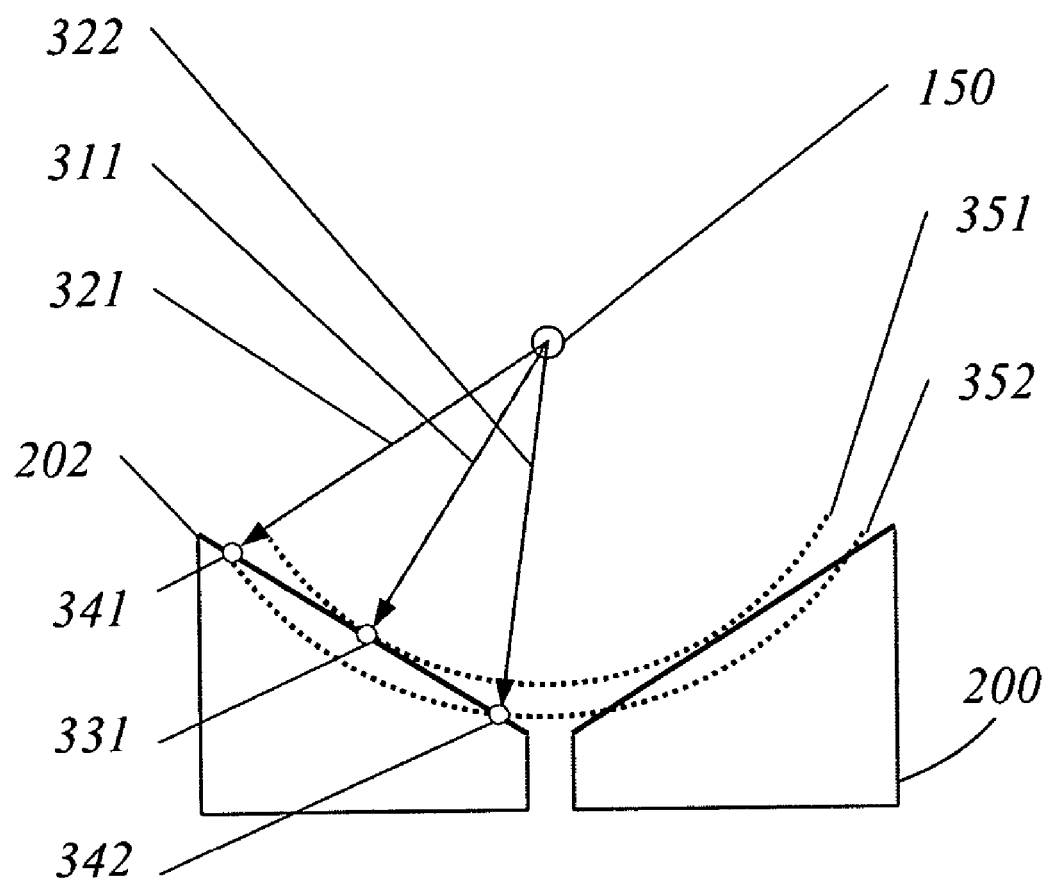
FIG. 4 is a schematic diagram illustrating the measurement concept for conical part surfaces.

Referring to FIG. 4, the local radius of curvature of the optical measurement surface is varied to contact conical part surface 202. The optical measurement surface is depicted contacting part surface 202 for two difference radii of curvature: first optical measurement surface 351 and second optical measurement surface 352. These positions of the optical measurement surface correspond to two different positions of OPD translation stage 134 (see FIG. 1). First optical measurement surface 351 contacts part surface 202 at intersection point 331. Also shown is a chief ray 311, which indicates the illumination and imaging path for intersection point 331. Note that chief ray 311 is substantially perpendicular to part surface 202 (i.e., the optical measurement surface tangentially contacts part surface 202 at point 331), which is the ideal condition for maximum light return and maximum sensitivity to deformations in part surface 202. Two additional intersection points 341 and 342 show where second optical measurement surface 352 makes optical contact with part surface 202. Here two chief rays 321 and 322 corresponding to intersection points 341 and 342 are at near to normal incidence but at different angles and having different lengths than chief ray 311.

Figure 5:
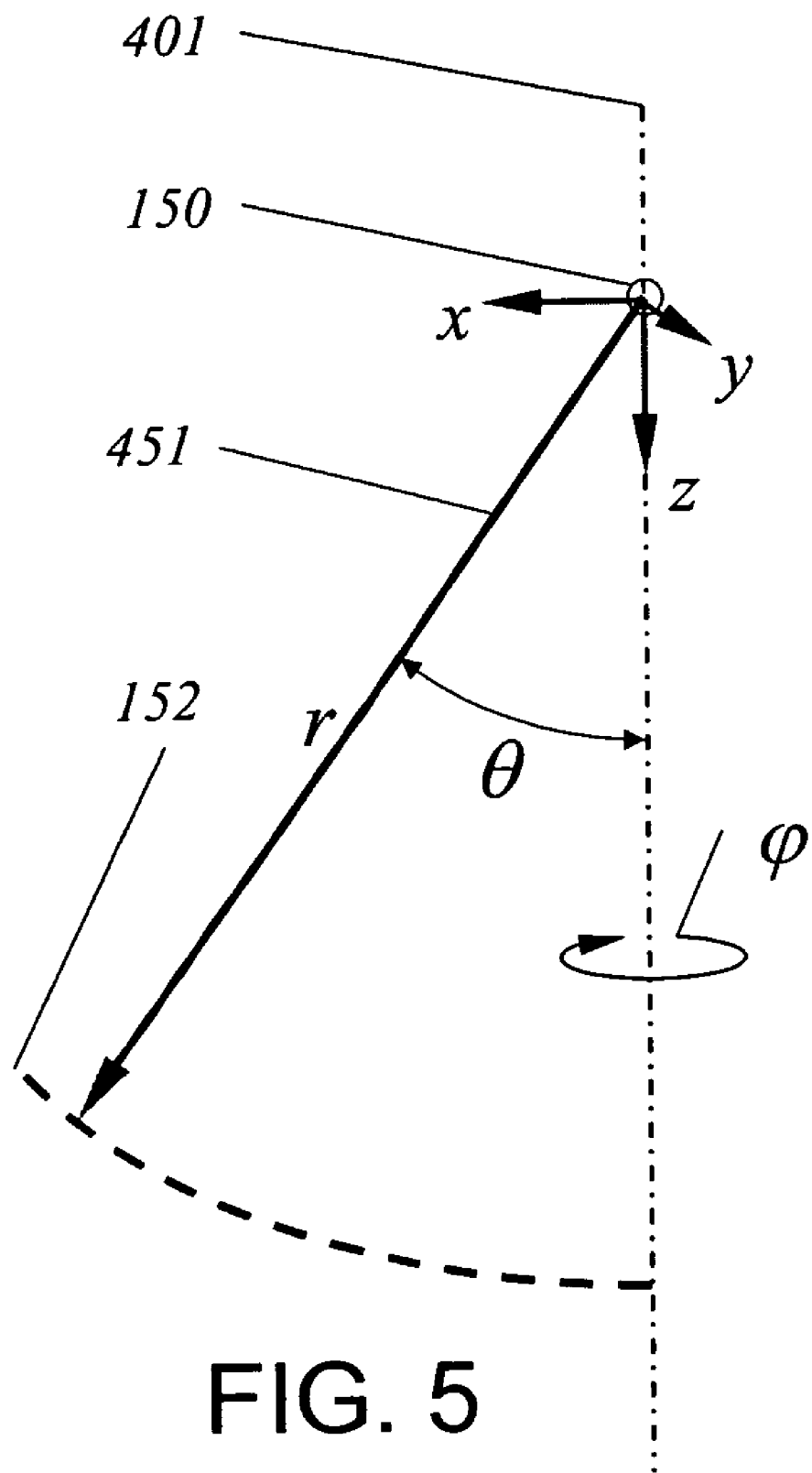
FIG. 5 shows the ray geometry and coordinate detail.
Figure 6:
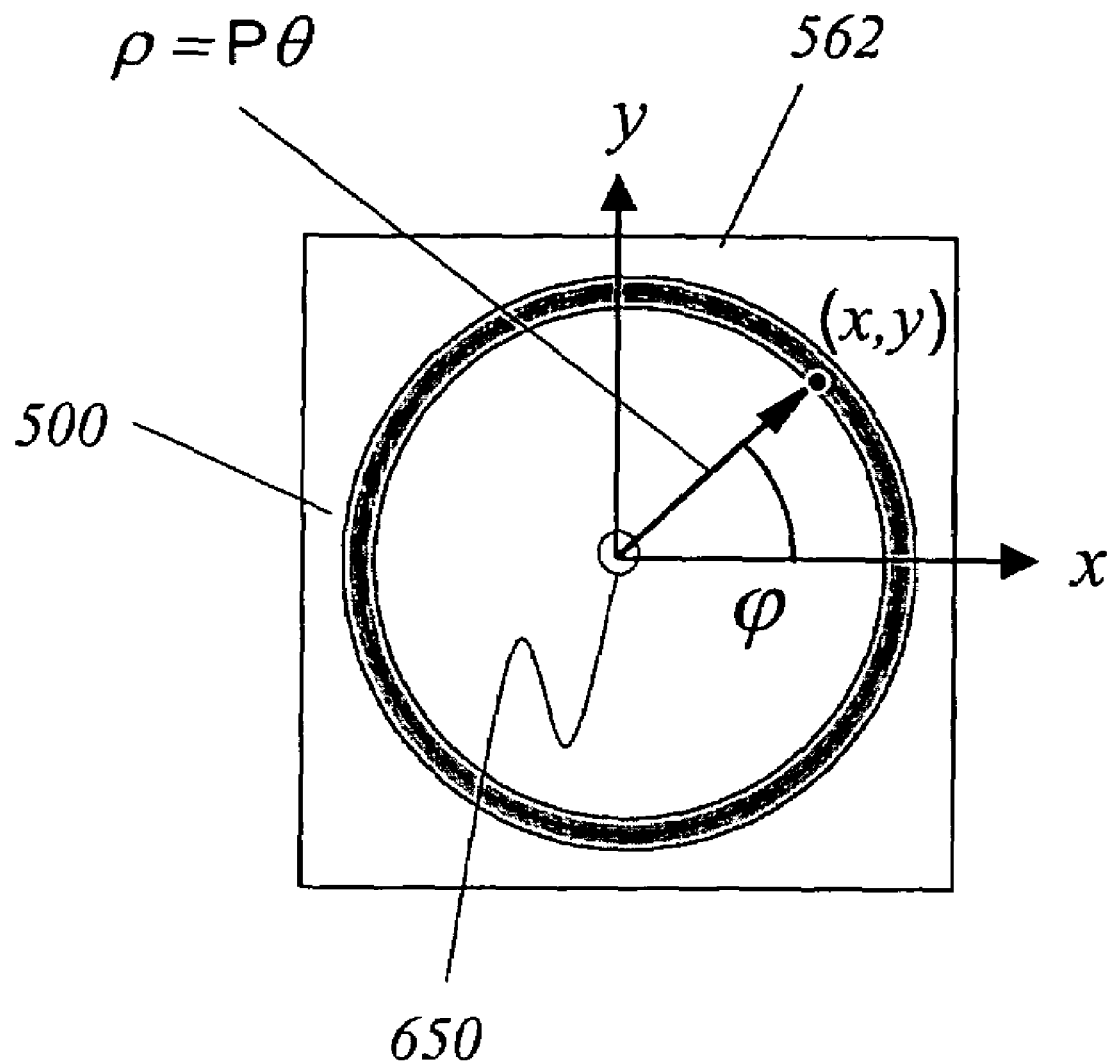
FIG. 6 shows the coordinate mapping to camera image.

FIG. 5 is a further detail drawing of the measurement geometry, showing the angles and lengths of a specific chief ray 451 similar to chief rays 321 and 322 shown in FIG. 4. We define the inclination or chief ray angle $\theta$, the azimuthal angle $\phi$, the ray length r from measurement datum point 150 to optical measurement surface 152, and the Cartesian coordinates x, y, z. When measurement surface 152 is substantially spherical, ray length r is the same as the radius of the corresponding virtual sphere. FIG. 6 shows how the chief ray angle, $\theta$, and azimuthal angle, $\phi$, maps onto a flat-field image 560 on a camera area 562. The mapping typically involves a coordinate transformation that may for example be $$\rho = P\theta \tag{1}$$

where $\rho$ is the radius on the camera image with respect to a central datum point projection 650 at the image and P is a substantially fixed scaling factor. Because the imaging system causes the chief ray angle, $\theta$, to map to the same image radius while the OPD is varied, the magnification of the system is constantly changing during the scan of the optical measurement surface. This behavior is very different from the more common telecentric imaging, for which one seeks to maintain constant magnification for a range of object positions. The direct result from a measurement is therefore a collection of measured radii r as a function of the chief ray angle θ and azimuthal angles, φ. Many other mappings are possible, depending on the optical properties of sensor 100.

A variety of interferometric distance measurement techniques can be used to determine ray length r, including e.g., monochromatic and multiple-wavelength laser interferometry, phase-shifting interferometry, infrared interferometry, and low coherence interferometry.

Figure 7:
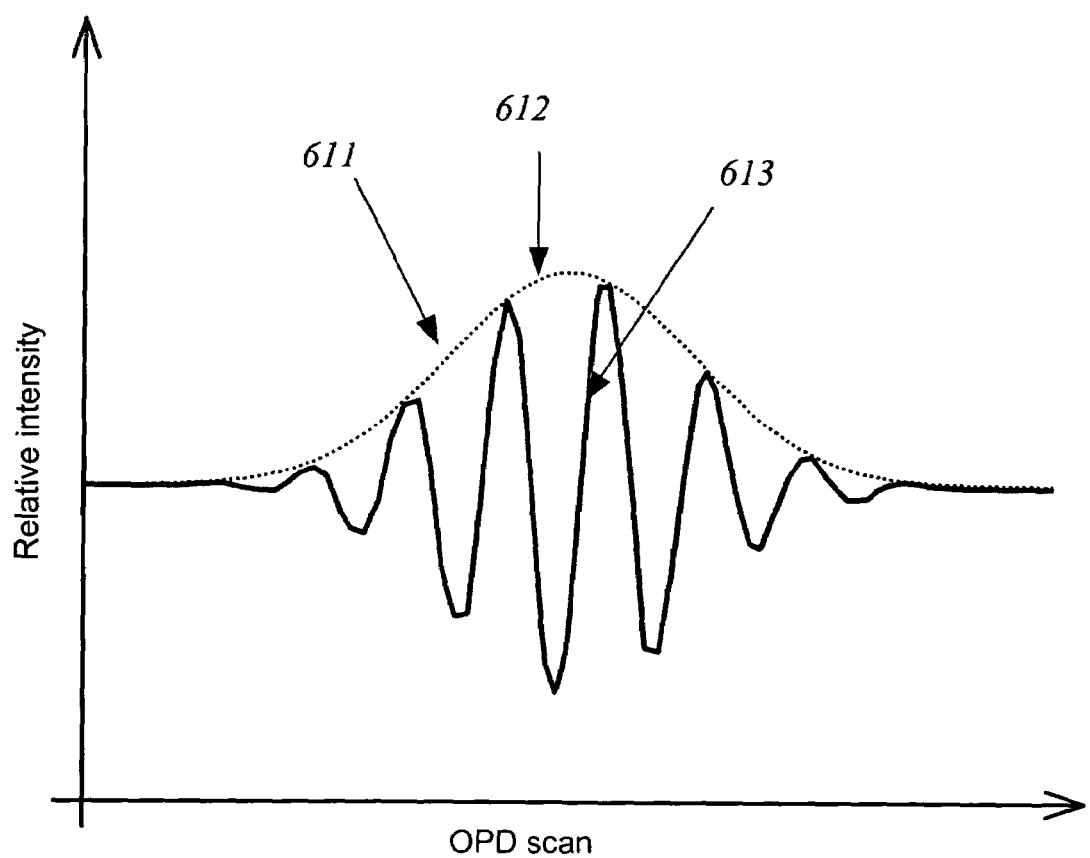
FIG. 7 is a plot of relative intensity of a pixel as a function of optical path difference (OPD)

In the low coherence interferometry approach, the measurement process is similar to that used with a scanning white light interferometer (SWLI). An example data set acquired for a single camera pixel using a SWLI process is shown in FIG. 7. The localization of an interference intensity signal 613 around the zero OPD position is characteristic of interferometry assuming that source 110 (see FIG. 1) is spectrally broadband, e.g., has a spectral bandwidth of 100 nm centered at 600 nm. The fringe localization provides a means for determining the precise moment when the optical measurement surface intersects the object point corresponding to the image pixel. The scan motion is precisely controlled, so that knowledge of when a given object point is at zero OPD can be directly translated into a ray length r. One can apply any of a variety of techniques for determining surface height using low-coherence sources. Suppose for example interference data for a first pixel looks as in FIG. 7, with a peak 612 in the fringe contrast 611 at a scan position of 0 µm. A second pixel might have a different fringe contrast peak at a different scan position, for example 10 µm. The difference in radius r between the two object points corresponding to these image pixels would therefore be 10 µm. The data processing involves, e.g., coherence envelope detection or frequency domain analysis, as described by T. Dresel, et al. in *Applied Optics* Vol. 31, pp. 919–925 (1992) and U.S. Pat. No. 5,398,113, respectively.

Figure 8:
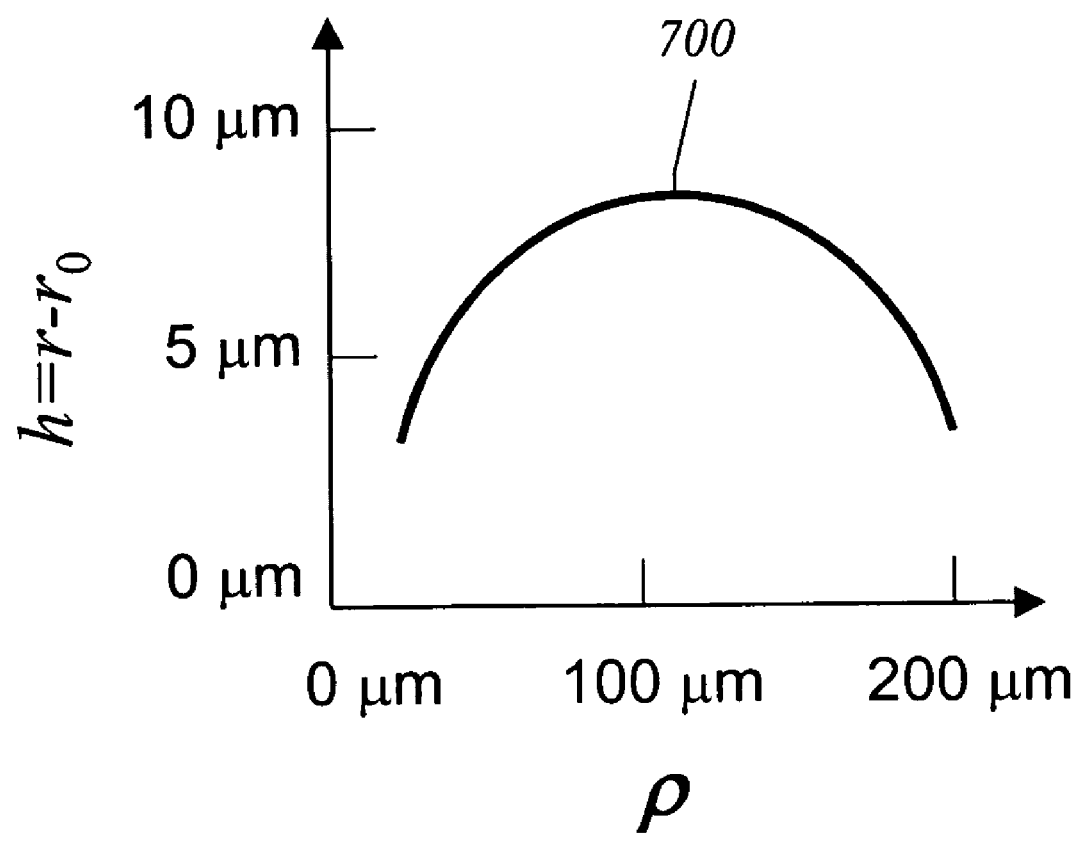
FIG. 8 is a plot showing a radial cross section profile through the height data.

Computer 199 records interference images while varying the OPD. From these images, computer 199 determines $r(\theta, \phi)$ data. From this data, computer 199 generates radial height profiles along different azimuthal directions. Each datum in a radial height profile corresponds to the difference between part surface 202 and optical measurement surface 152 at a particular radius of curvature along a normal to optical measurement surface 152 at the particular radius of curvature. A radial height profile 700 is illustrated in FIG. 8.

Figure 9:
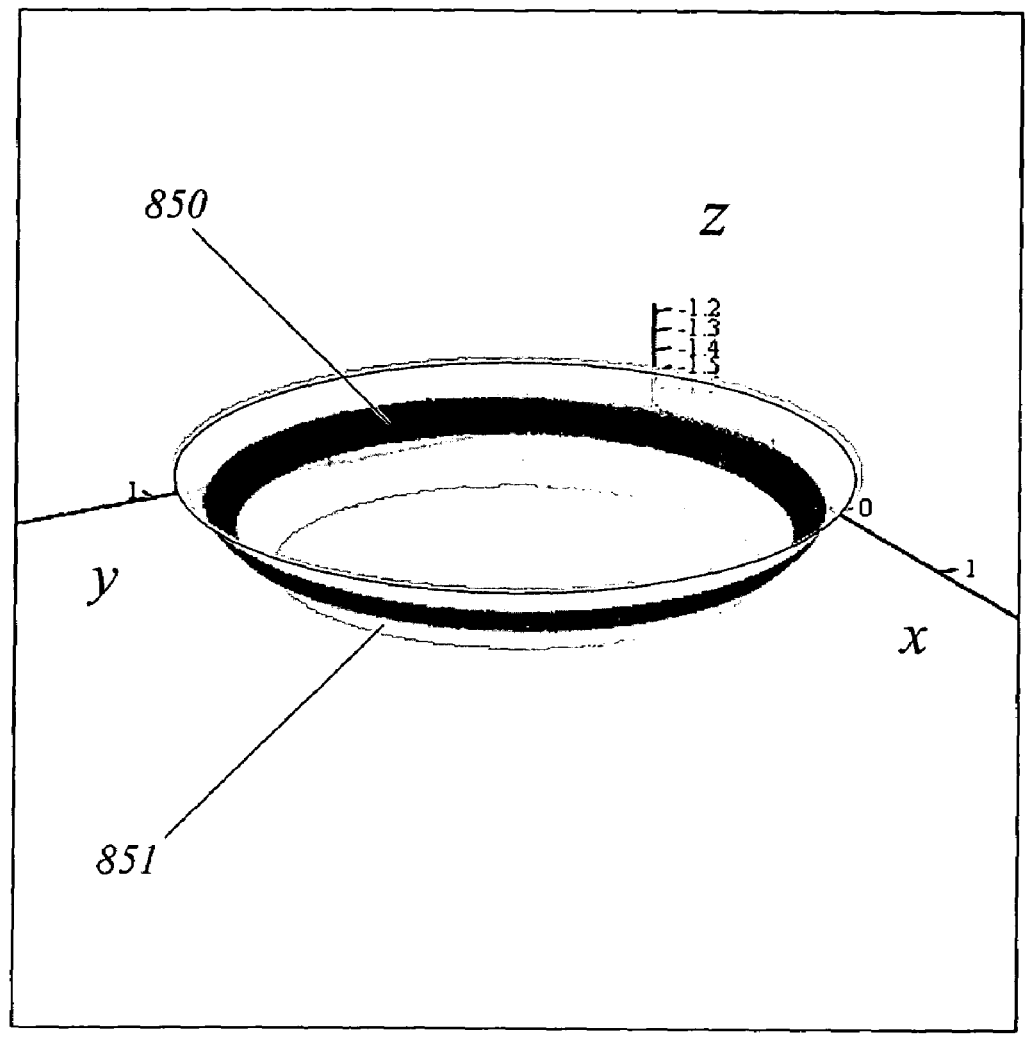
FIG. 9 is a 3D representation of acquired data using a Cartesian coordinate system.

Referring to FIG. 9, radial height profile data is transformed from the r, θ, φ coordinate system to a 3D representation 850 in a more familiar x, y, z Cartesian coordinate system, using e.g., $$x = r \sin(\theta)\cos(\phi)$$

$$y = r \sin(\theta)\sin(\phi).$$

$$z = -r \cos(\theta) \qquad (2)$$

Figure 10:
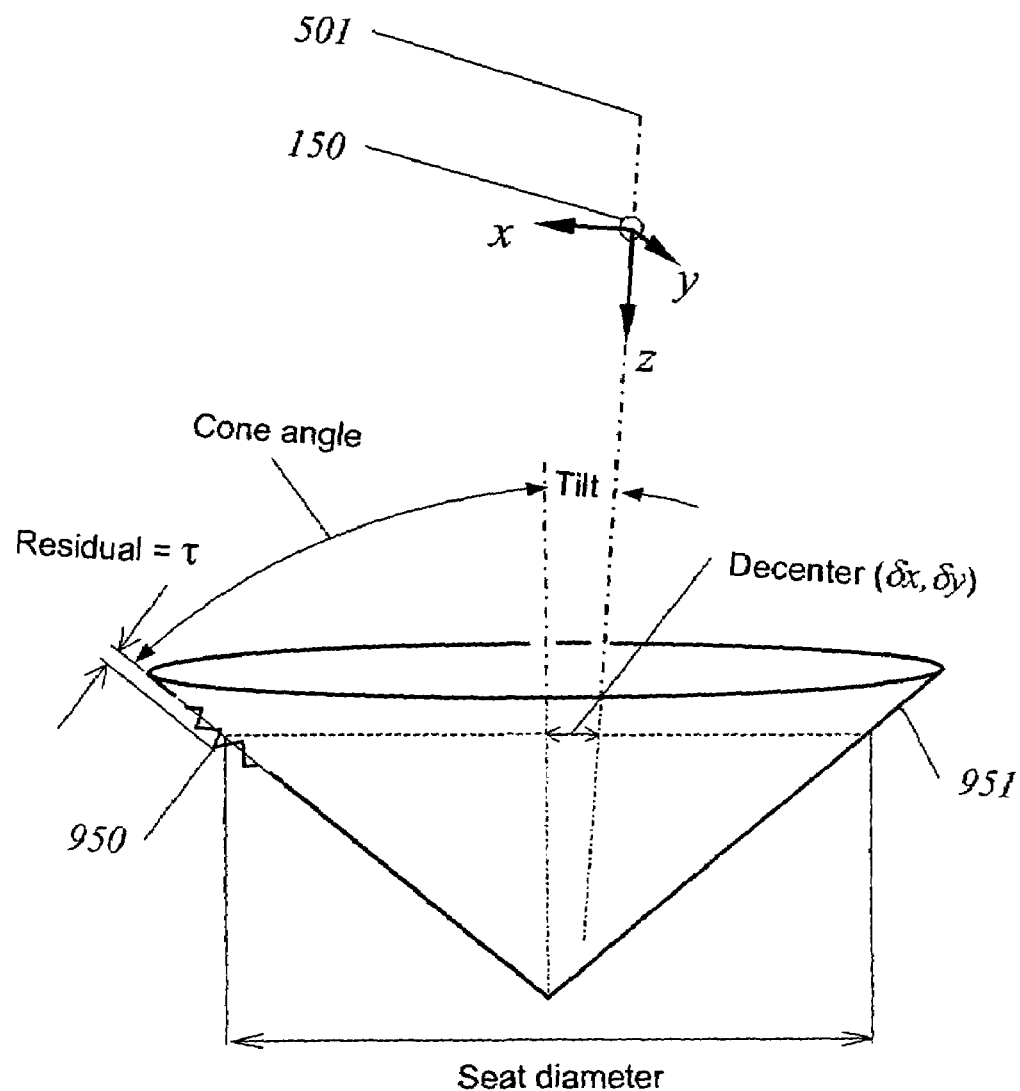
FIG. 10 shows parameters used when fitting a theoretical cone to data.

Using, e.g., a nonlinear least-squares fit, a best-fit theoretical surface 851 is fit to 3D representation 850. Several parameters are extracted from best-fit theoretical surface, including cone angle, decenter of the cone with respect to the instrument optical axis, axis orientation (i.e., tilt) with respect to the instrument optical axis, and location of a specific diameter, e.g. a valve seat diameter, with respect to the 3D representation 850. Referring to FIG. 10, a residual profile τ is also calculated with respect to the best-fit theoretical cone 951 corresponding to a 3D data set 950. The residual profile is the deviation of measured part surface 202 from best-fit theoretical surface 851.

Figure 11:
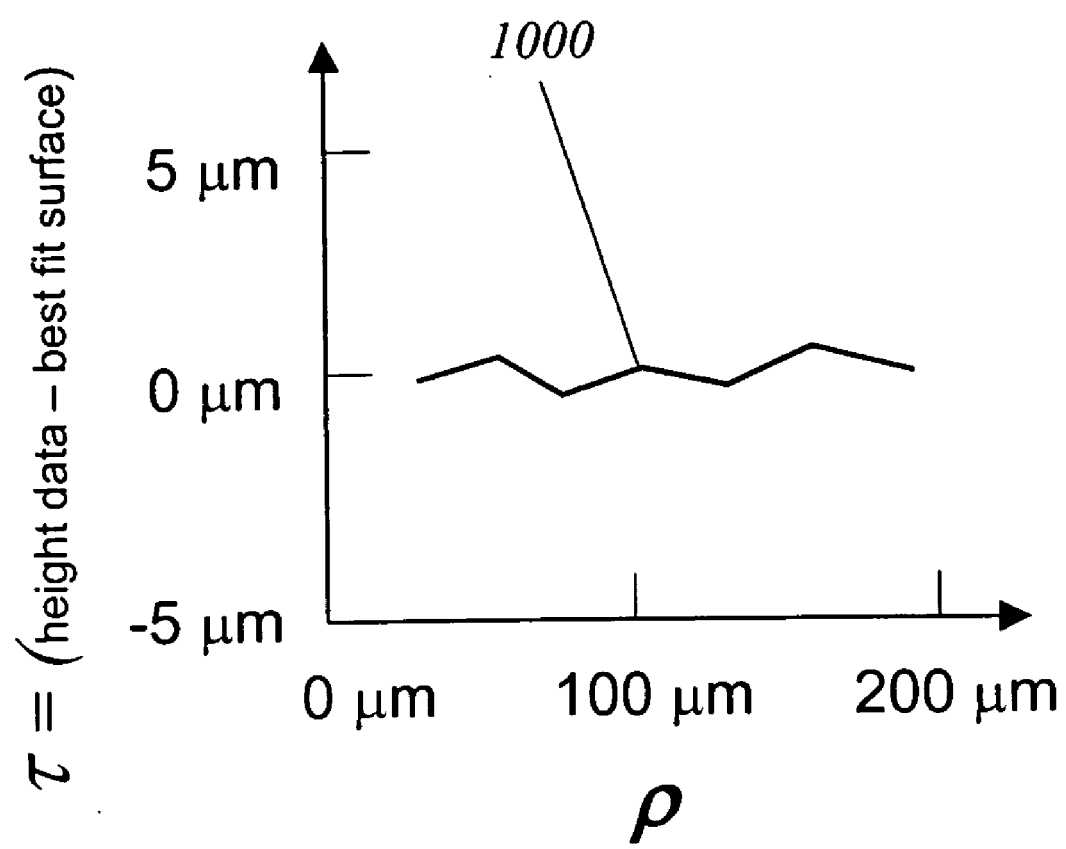
FIG. 11 is a plot showing a radial cross section profile through residual data, after subtraction of best-fit cone.

Once the $\tau(\theta, \phi)$ data are generated by the preceding analysis, a data cross-section in an azimuthal direction shows a deviation profile 1000 as illustrated in FIG. 11. A deviation profile is the difference between part surface 202 and the theoretical best-fit cone to height data representative of part surface 202.

Figure 12:
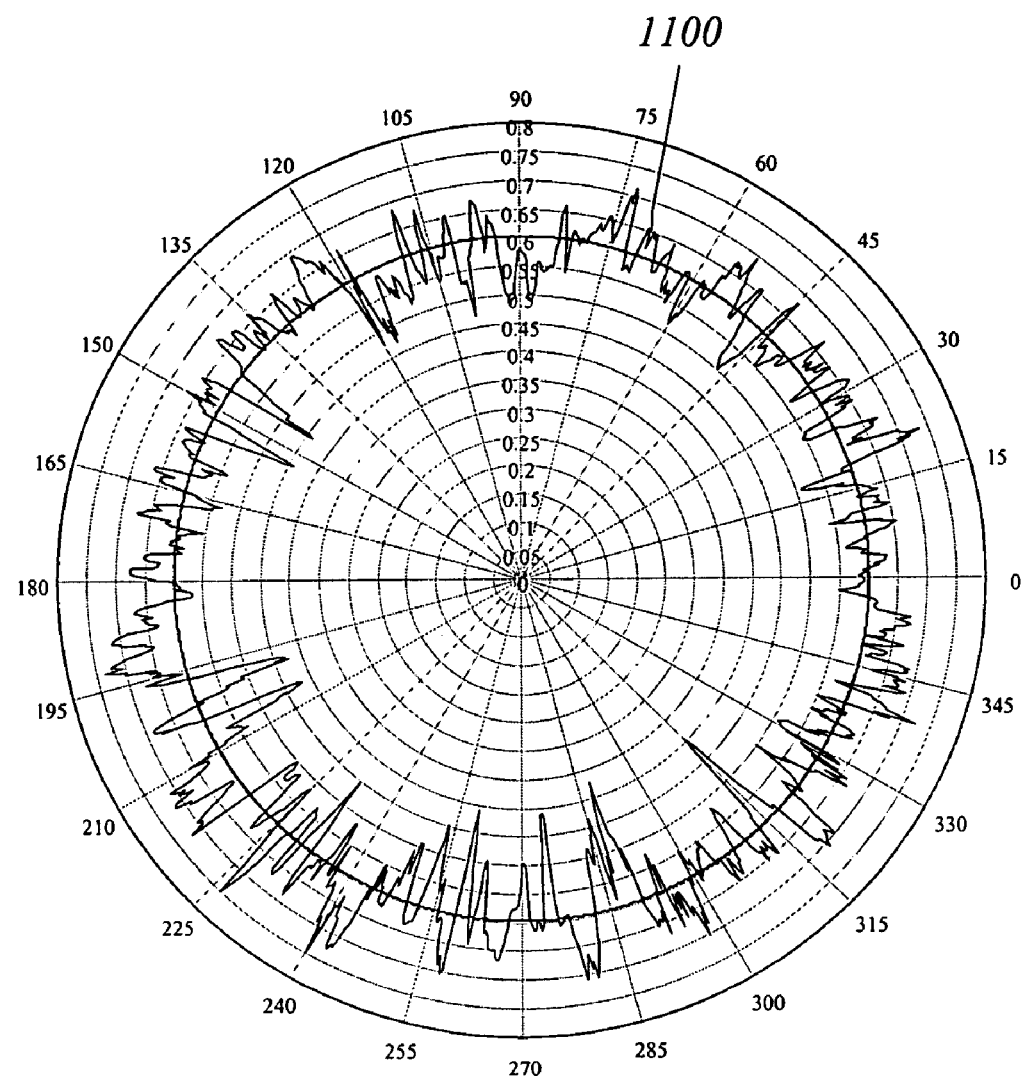
FIG. 12 is a plot showing a roundness profile of residuals (after fit subtraction)

Referring to FIG. 12, computer 199 also determines the deviation of the part surface from the best-fit cone for a circular slice through the best-fit cone at a selected diameter value. The resulting roundness profile is a familiar format to users of stylus gages. This profile represents the variation in length of normal-incidence vectors originating at a virtual datum point on the axis of the best-fit cone. Equivalently, the straightness profile shown in FIG. 11 represents the deviation of the part surface from the ideal fitted conical surface.

Figure 13:
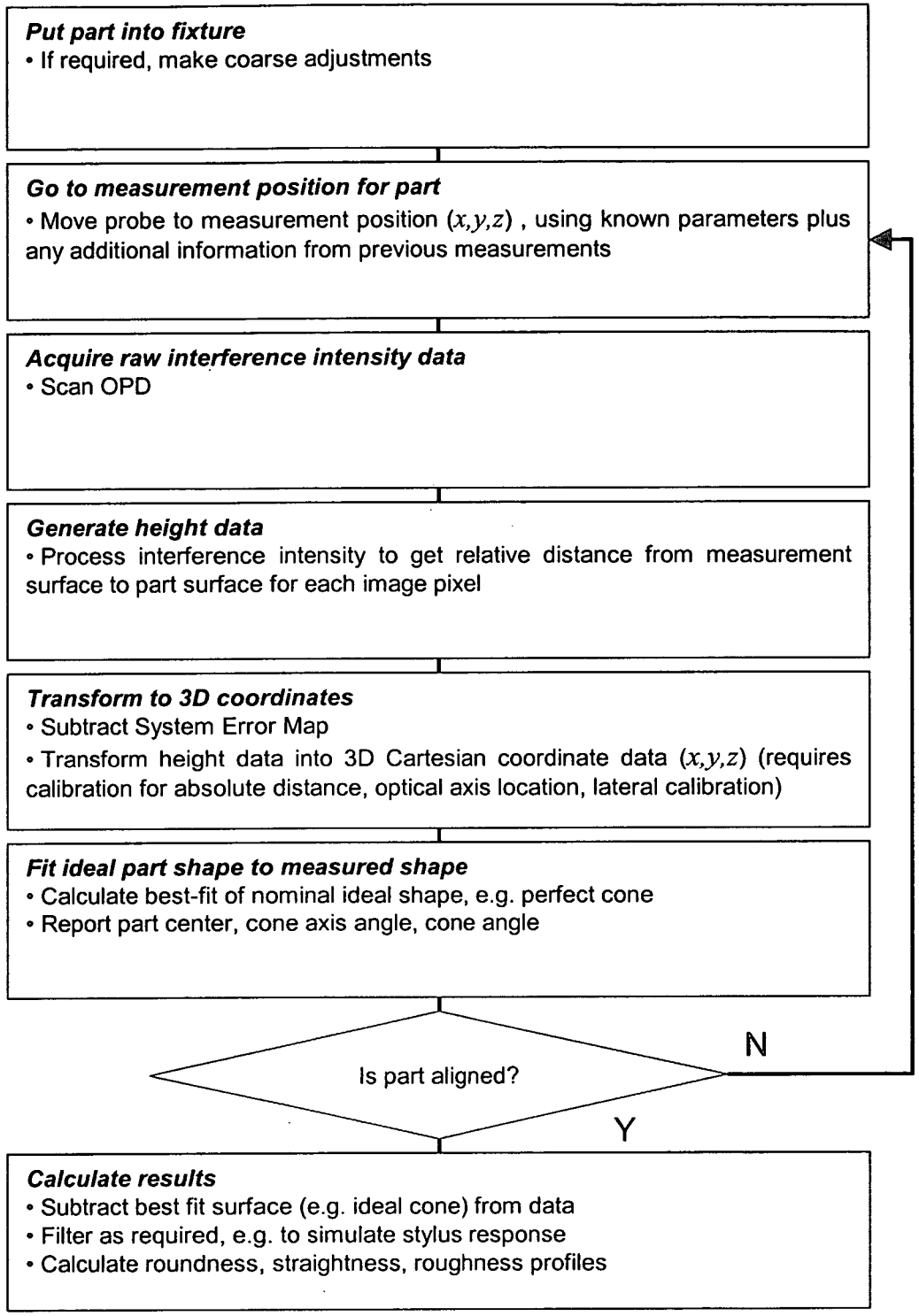
FIG. 13 is a flow chart of a part measurement cycle.

FIG. 13 is a flowchart summarizing a part measurement cycle, including an iterative alignment procedure. After placing a part in the part fixture, the system positions the part relative to the sensor using known positioning parameters and any additional information from previous measurements. Once in position, the system varies the OPD of reference and measurement wavefronts, causing the optical measurement surface to contact a part surface. While the OPD is varied, the system records interference patterns imaged on the detector. The computer then processes the intensity at each pixel as a function of OPD to locate pixels corresponding to chief ray angles at which the optical measurement surface contacted the part surface. The computer then determines a radial height profile based on the relevant pixels. One then provides a System Error Map, which includes any theoretically and/or empirically determined systematic errors present in the system, and then subtracts the System Error Map from the radial height profile. Then, the computer transforms the radial height profile into 3D Cartesian coordinate data, reconstructing the measured portion of the part surface. Subtracting the System Error Map from the data compensates for these errors in the analysis.

One way of establishing a system error map is by measuring a known spherical mirror. If measurement optics 130 and reference optics 140 are optically identical and perfectly aligned with respect to each other, one would expect to measure a map where the surface deviation is zero everywhere (contrary to a cone). In this situation, any measured height deviation represents a small system imperfection that can be corrected to first order by subtracting this measured map from subsequent cone measurements. If the spherical mirror is not perfect, its shape (for example known from a Fizeau interferometer measurement) can be subtracted from the system error map.

Accordingly, the 3D Cartesian coordinate data is compensated for these systematic errors, and provides a user with an accurate rendering of the actual part surface. The computer then calculates a best-fit shape to the 3D Cartesian coordinate data, and extracts parameters associated with the parts position relative to the sensor from the best-fit shape. Based on these parameters, the computer and/or user decide whether the part is sufficiently aligned. If the part is not aligned, the position of the part is adjusted and the measurement cycle repeated. If the part is aligned, the computer proceeds with a more detailed characterization of the part surface based on the acquired data.

Accurate calibration of the instrument facilitates proper interpretation of the data. Calibration includes, e.g., determining the exact location of the point datum and of the absolute radius of the measurement sphere.

Figure 14:
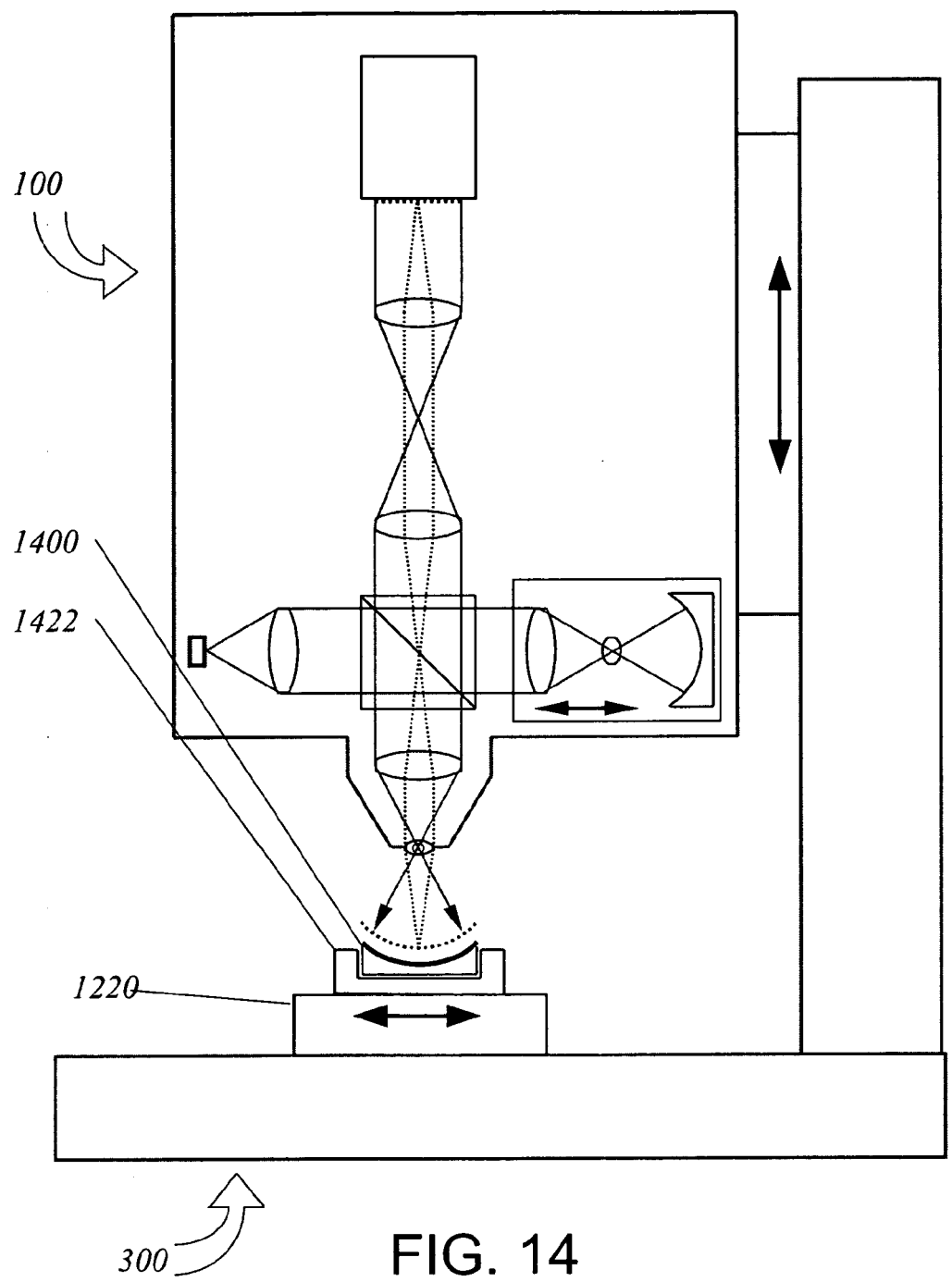
FIG. 14 shows the interferometry system of FIG. 3 with a calibration artifact.
Figure 15:
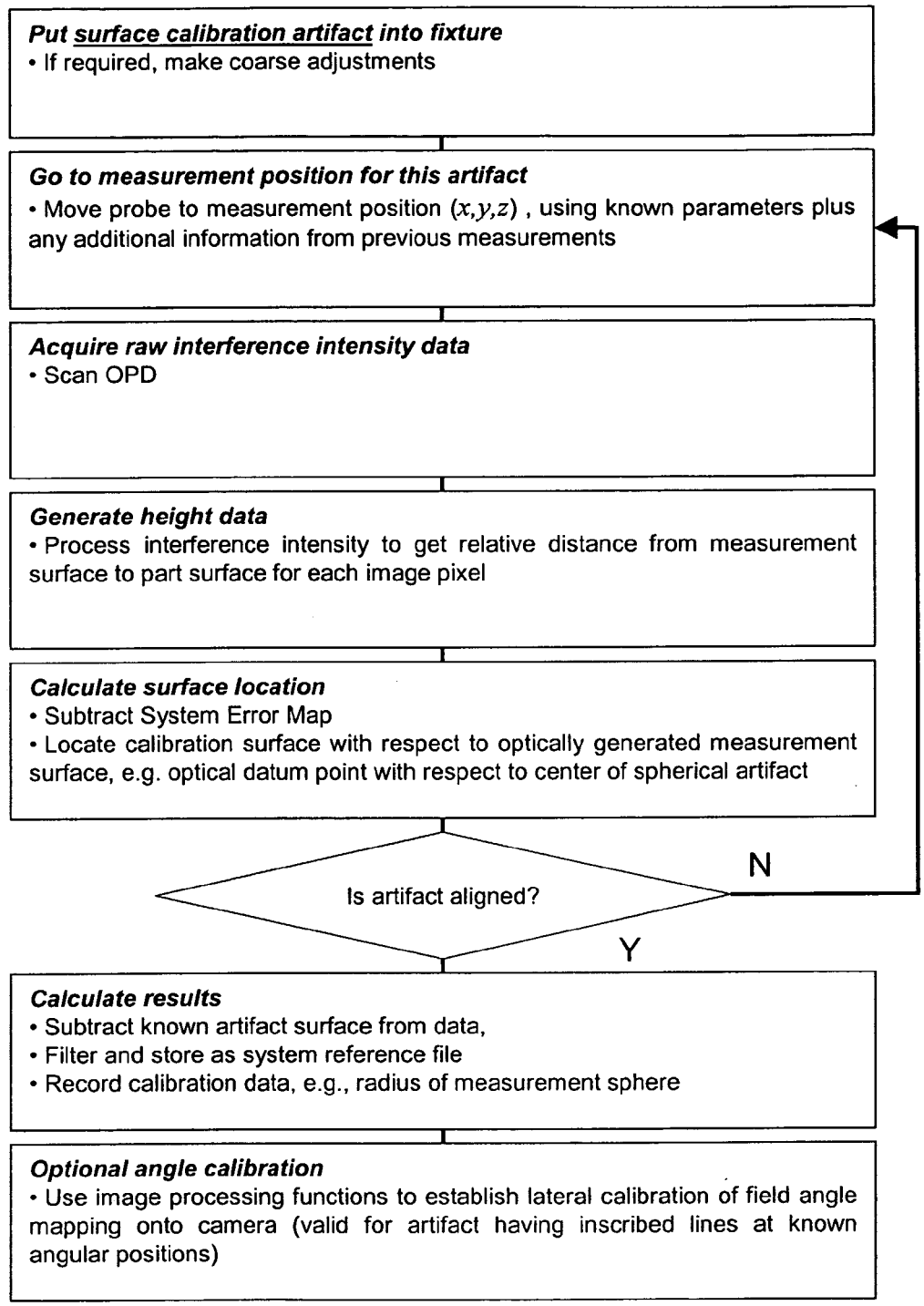
FIG. 15 is a flow chart of a measurement surface calibration cycle.

For calibration of the overall shape of the optical measurement surface, it is useful to have an appropriate calibrated artifact. For example, a spherical artifact of known radius facilitates these calibrations for a spherical optical measurement surface. FIG. 14 illustrates such a calibration procedure involving a spherical artifact 1400 carried by an artifact fixture 1422 for system 300. Note that artifact fixture 1422 is positioned using x, y stage 1220. x, y stage 1220 support both part fixture 1222 and artifact fixture 1422, for easy switching between surface calibration and measurement. Because spherical artifact 1400 has a known radius of curvature, this calibration provides an absolute radius reference, allowing sensor 100 to measure absolute part diameters accurately, rather than simply deviations, e.g., from roundness. FIG. 15 is a flowchart summarizing a measurement datum point location calibration cycle, including an iterative alignment procedure.

Figure 16:
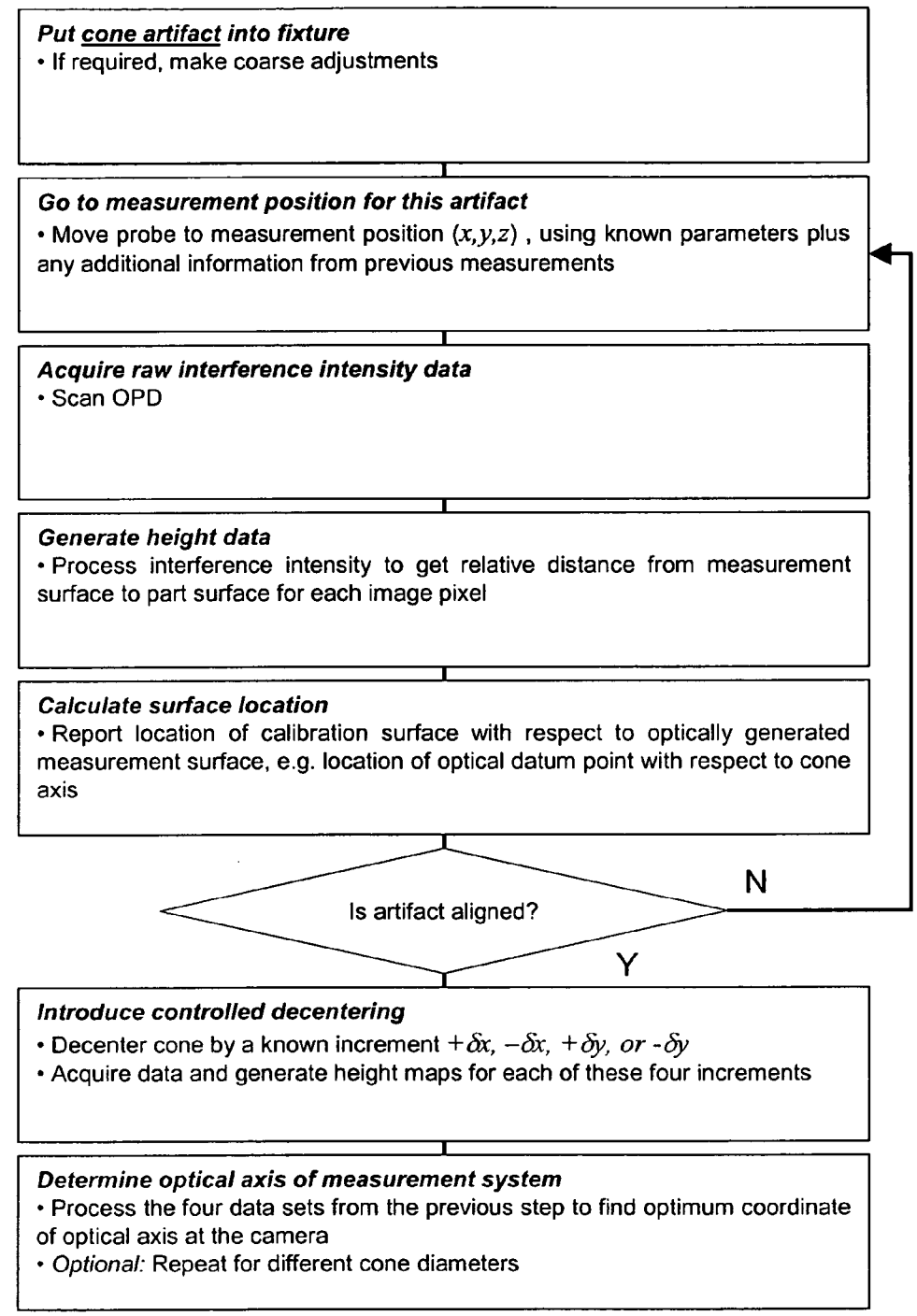
FIG. 16 is a flow chart of a datum point calibration cycle.

For determining the exact location of measurement datum point 150 with respect to sensor 100, it may be preferable to use a conical artifact instead of, or in addition to, spherical artifact 1400. FIG. 16 summarizes such a procedure. The initial measurement sequence is analogous to the measurement sequence described above for a part surface (see, e.g., FIG. 13), however, as the cone shape is already known there is no need to determine a best-fit surface to the 3D Cartesian coordinate data. Instead, the computer calculates the position of the known surface with respect to the measurement datum point. Once the artifact is sufficiently aligned, the system decenters the artifact with respect to the measurement datum point and acquires a new set of data for the decentered artifact. This is repeated for four times, corresponding to decentering by incremental amounts δx, −δx, δy, and −δy. For each data set, the computer fits the known cone shape to the data for multiple locations of center point 650 and selects the location corresponding to the smallest deviation of the cone reconstructed in Cartesian space with respect to the known cone shape. Hence, each data set yields an optimum position for point 650. The mean of these optimum positions is used as a best estimate of the true projection of the optical axis onto the detector. Of course, this process can be performed using fewer (or more) than four measurements. Multiple measurements help to compensate for any anomalies or defects in the shape of the conical artifact.

Figures 17A, 17B:
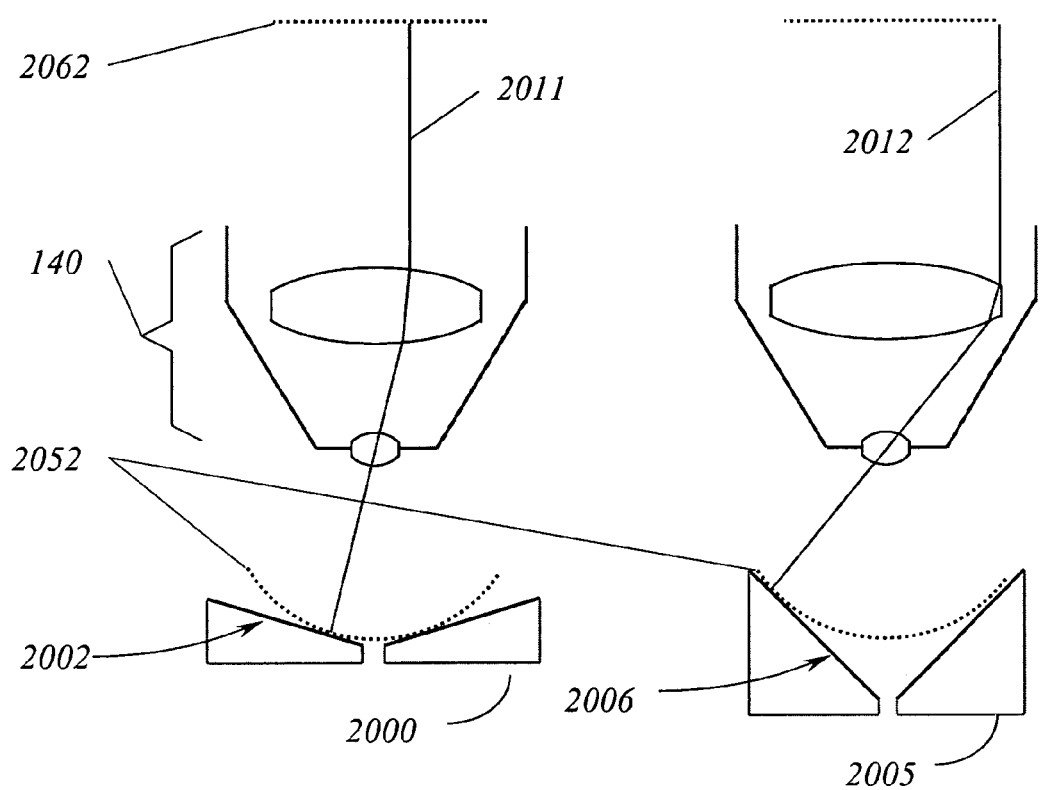
FIG. 17(a) shows a shallow cone measurement with an interferometry system.
FIG. 17(b) shows a steep cone measurement with the interferometry system of FIG. 17(a)

FIGS. 17(a) and 17(b) illustrates the flexibility of the measurement geometry with respect to cone angle. FIG. 17(a) shows a part 2000 with a shallow conical surface 2002 (e.g., cone angle greater than 90°) positioned relative to optical measurement surface 2052. A chief ray 2011 travels down at normal incidence to the shallow part surface 2002 and reflects back through measurement optics 140 to a nominally flat intermediate real image 2062. FIG. 17(b) shows a part 2005 with a steep conical surface 2006 (e.g., cone angle less than 90°) positioned relative optical measurement surface 2052. A chief ray 2012 passes through measurement optics 140 and reflects back to intermediate real image 2062, but at a different location corresponding to a different image radius p to shallow conical surface 2002.

Figures 18A, 18B:
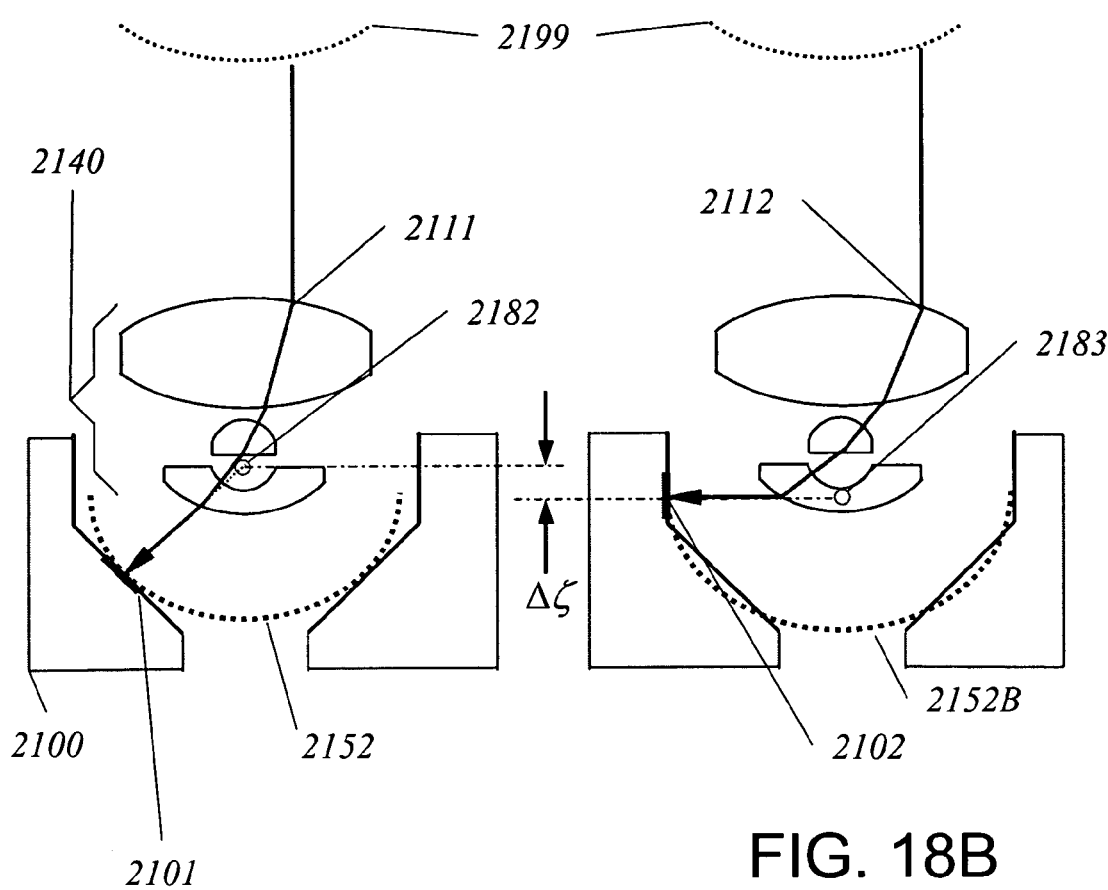
FIG. 18(a) shows a conical surface measurement with an interferometry system.
FIG. 18(b) shows a cylindrical surface measurement with the interferometry system of FIG. 18(a)

It is feasible for a measurement to include capturing data from other surfaces to serve as datums on the object itself. For example, it may be important to know the location and orientation of the cone with respect to a surrounding cylindrical bore or some other feature, e.g., the runout of the cone with respect to an axial datum established by the cylinder. The data capture can take place simultaneously with the measurement of the cone, or involve a two-step process that includes a precise displacement of the optical point datum between measurements. For example, FIGS. 18(a) shows wide-angle measurement probe optics 2140 located relative to a part 2100 having conical and cylindrical portions. Optical measurement surface 2152A contacts part 2100 at conical portion 2101. Wide-angle measurement probe optics 2140 image a reflected chief ray 2111 to an image surface 2199. Varying the OPD allows one to measure the distance of conical portion 2101 from measurement datum point 2182. In FIG. 18(b) optical measurement surface 2152B contacts part 2100 at cylindrical portion 2102. Wide-angle measurement probe optics 2140 also image a chief ray 2112 reflected from portion 2102 to image surface 2199. In this instance, varying the OPD allows one to measure the distance of cylindrical portion 2102 from displaced measurement datum point 2183. Due to an axial aberration, displaced measurement datum point 2183 is shifted from measurement datum point 2182 by an amount $\Delta\zeta$ in the z-direction. This displacement can be accommodated for in offline data analysis by replacing z in Eq. 2 with $z'=z+\Delta\zeta$. Note that in this case, the resultant wide-angle measurement surface 2152 is not necessarily a perfect sphere and does not necessarily map to a flat intermediate real image 2199, the ray angles being perhaps too severe. The remaining distortion may be corrected by optics elsewhere in the system.

Figures 19A, 19B:
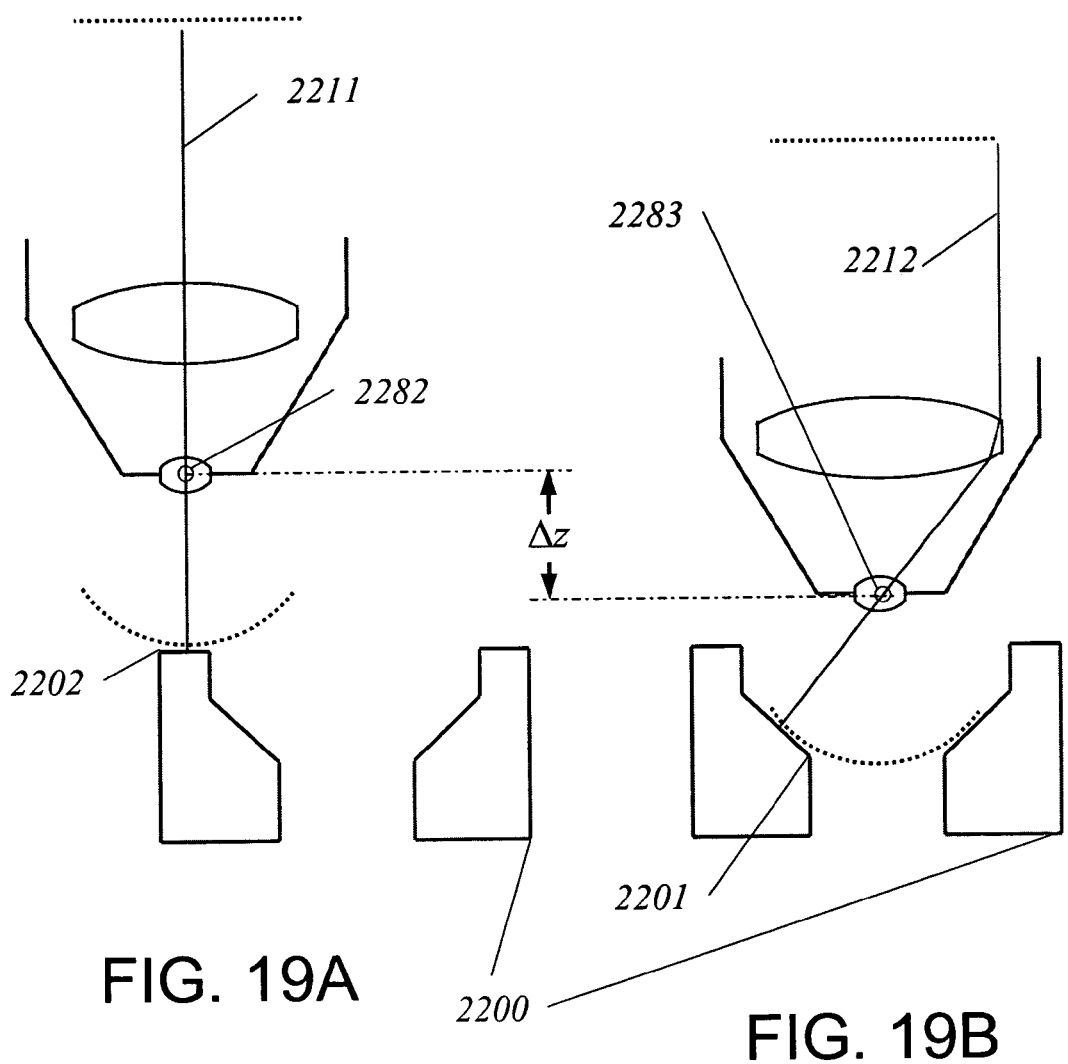
FIG. 19(a) shows referencing an interferometry system to a horizontal flat datum for height measurements.
FIG. 19(b) shows measuring a conical surface with the interferometry system of FIG. 19(a)

FIGS. 19(a) and 19(b) show another example of datum referencing, this time to a horizontal surface. For this application, precision z-axis and x, y-stages translate measurement optics 140 relative to a measurement part 2200. Referring specifically to FIG. 19(a), the system first measures the location of a datum surface 2202 on a datum-referenced part 2200, using a first measurement point datum 2282. A chief ray 2211 traces an exemplary optical path for this configuration. Referring to FIG. 19(b), after a controlled sensor displacement $\Delta z$ to provide a second measurement point datum 2283, the system measures a cone surface 2201. A chief ray 2212 shows an optical path for this configuration. The result of both measurements is a measurement of cone surface 2200 referenced in z to datum surface 2202. One can go further and reference the orientation, including tip and tilt, of cone surface 220 by making several z measurements at different locations on datum surface 2202.

Figure 20:
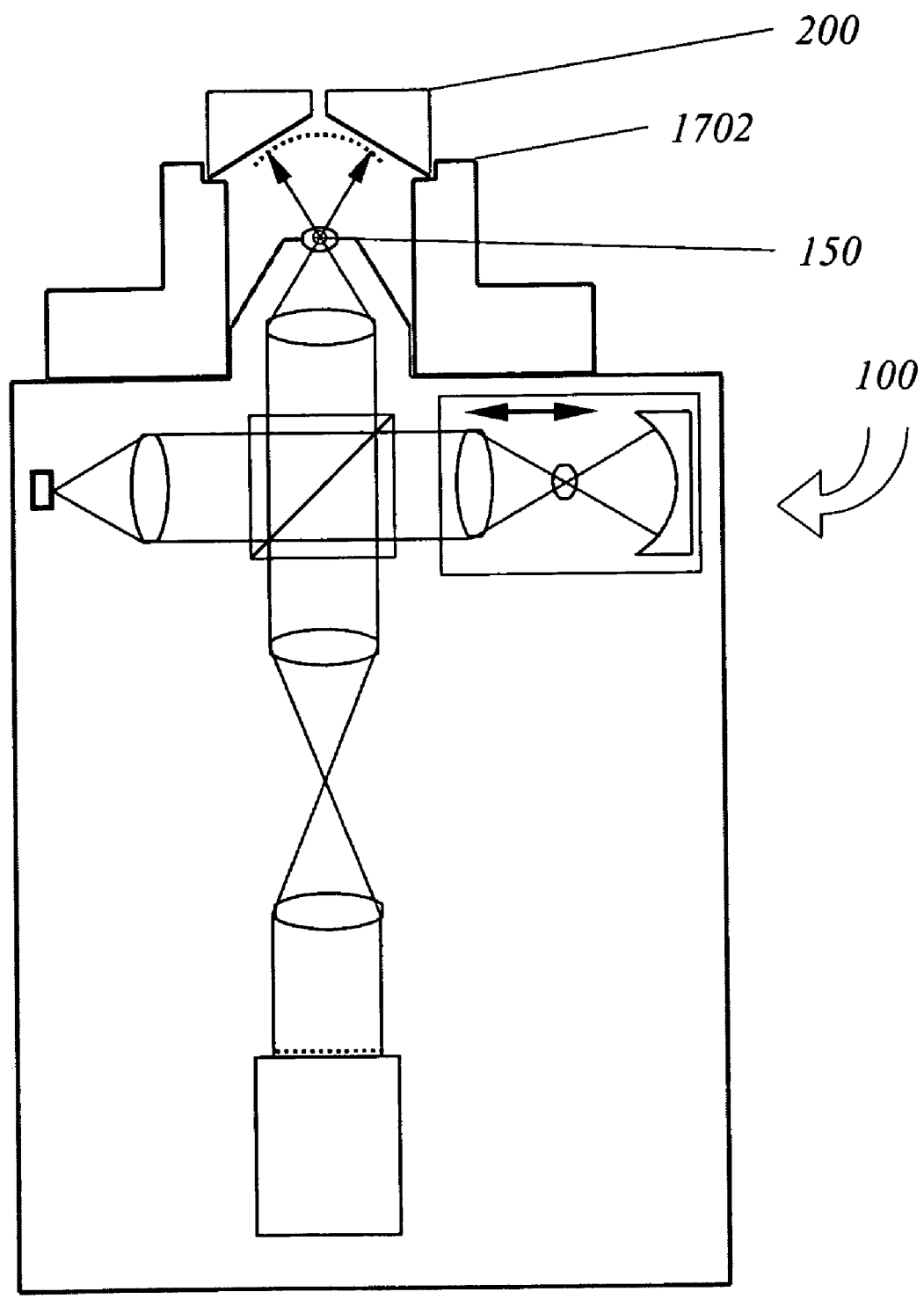
FIG. 20 is a schematic diagram of the sensor of FIG. 1 arranged in an upward-looking configuration with alignment by means of a precision part fixture.

While the present embodiment is configured with a sensor positioned above the part, other configurations can also be used. Referring to FIG. 20, a precision part fixture 1702 facilitates rapid alignment of part 200 with respect to sensor 100. Part fixture 1702 correctly positions part 200 along the z axis with respect to measurement datum point 150 with minimal decenter and tip and without motorized stage motions and iterative alignment. In this case, part 200 kinematically adjusts to precision part fixture 1702.

Figure 21:
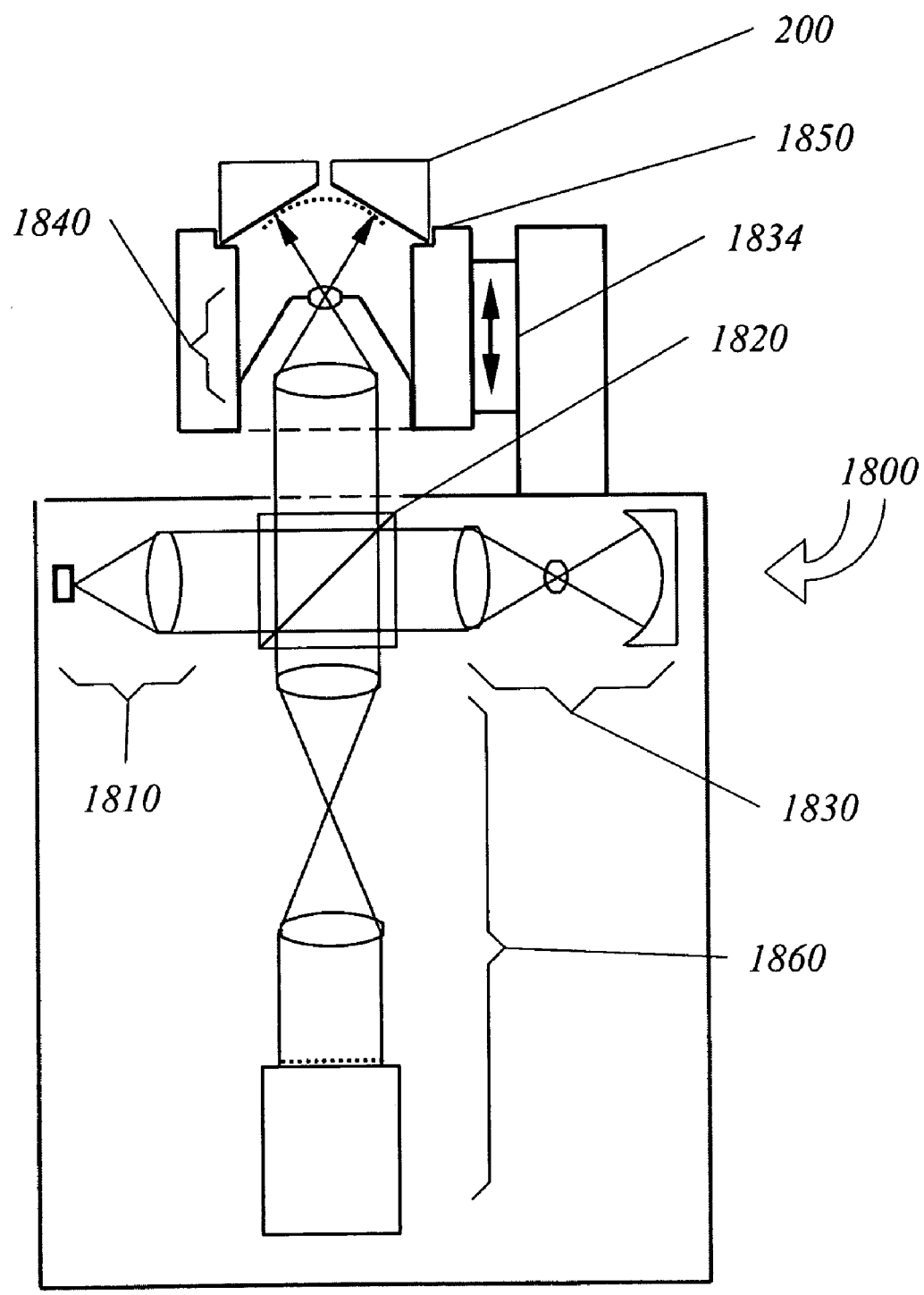
FIG. 21 is a schematic diagram of an upward looking sensor with OPD scanner on detachable measurement optics.

Sensor 100 can be modified to provide further functionality for accurately positioning and measuring complex surfaces. Referring to FIG. 21, a sensor 1800 includes detached measurement optics 1840, which is integrated into part fixture 1850. An OPD scan stage 1834 for measurement optics 1840 allows for a fixed reference arm 1830 instead of the scanned reference optics in the aforementioned embodiment. Thus measurement optics 1840 and part 200 move together. This scanning varies the OPD in a telecentric portion of the interferometer. Sensor 1800 maintains proper focus over a wider range of OPD positions than sensor 100. Sensor 1800 maintains focus because during downward (upward) translation of stage 1834 the optical measurement surface moves away from (towards) the measurement datum point. However, the measurement point datum simultaneously moves downward (upward) with the optical measurement surface. The net effect is that the optical measurement surface remains substantially at the same position with respect to the rest of the interferometer, maintaining focus over a larger range of radii of curvature (this is particularly the case when the magnification of the system is close to one). Maintaining focus over the OPD positions increases the lateral resolution capability of the sensor.

Figure 22:
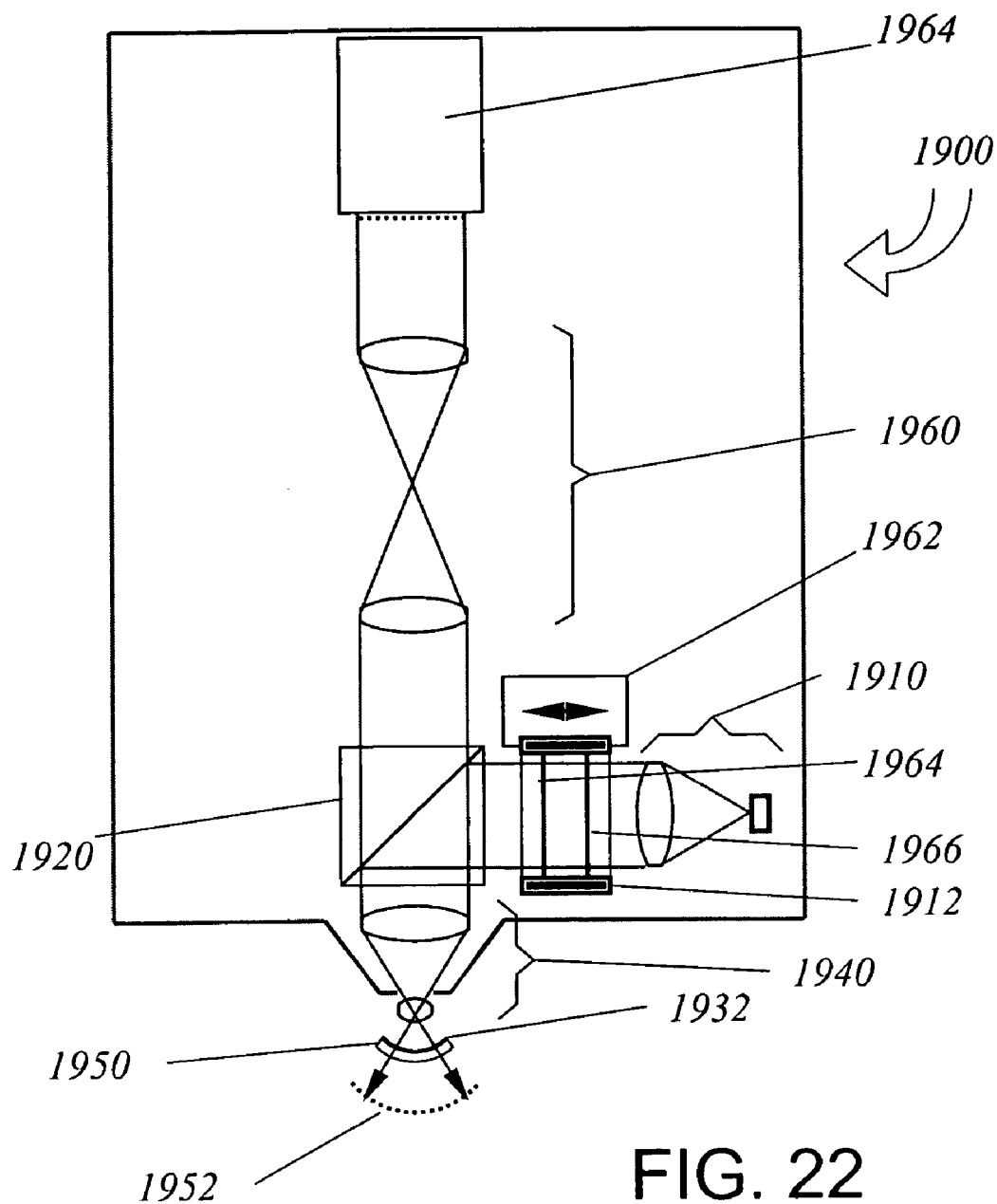
FIG. 22 is a schematic diagram of a sensor including a coupled Fizeau cavity.

Although the aforementioned embodiments include Linnik-type interferometers, other types of interferometer can be adapted for the same purpose. For example, FIG. 22 shows sensor 1900 that includes two Fizeau cavities operating in series. A local reference surface 1932 is positioned between measurement datum point 1950 and optical measurement surface 1952. A spectrally broadband illumination system 1910 illuminates a scanning Fabry-Perot etalon 1912. Etalon 1912 transmits a measurement wavefront, which is directed by a beamsplitter 1920 through measurement optics 1940 and reference surface 1932 to a measurement surface (not shown). A reference wavefront, on the other hand, is reflected once by etalon surfaces 1964 and 1966, before beamsplitter 1920 directs it through measurement optics 1940 to reference surface 1932. Reflected measurement and reference wavefronts are imaged via imaging optics 1960 to a detector. Additional reflections from the etalon give rise to additional combinations of measurement and reference wavefronts. Fabry-Perot etalon 1912 is mounted on a scanning stage 1962 that varies the OPD by varying the gap between etalon surfaces 1964 and 1966. A benefit of this configuration is that measurement and reference wavefronts share a mostly common path, meaning that small imperfections in e.g., measurement optics 1940 have nearly the same effect on both reference and measurement wavefronts. Sensor 1900 is effective for relatively small source sizes, such as super-luminescent diodes (SLD's), for high fringe contrast.

Figure 23:
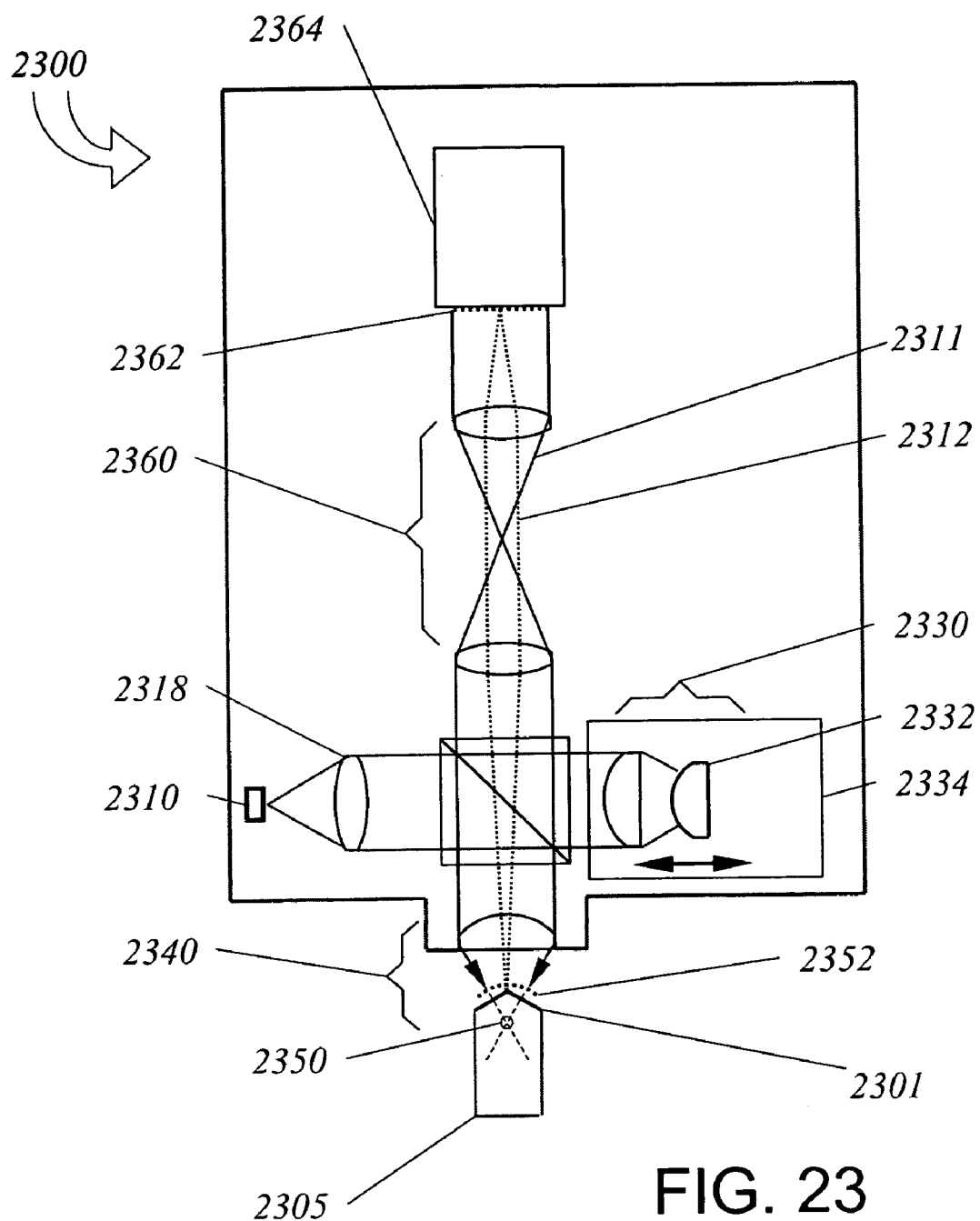
FIG. 23 is a schematic diagram of a sensor for external cone measurements.

In another embodiment, a sensor 2300 can image exterior cones, as shown in FIG. 23. The underlying principle is the same, in that an exterior cone surface 2301 is measured with respect to a measurement point datum 2350, in this case possibly falling within the interior of the part 2300, as shown. In this case, the imaging optics 2360 and measurement optics 2340 are positioned to properly focus a converging optical measurement surface 2352 back to a flat-field image 2362 on camera 2364, as indicated by the paths of a chief ray 2311 and a marginal ray 2212. This also entails a modification of the reference optics 2330 and the reference surface 2332 that are translated by OPD translation stage 2334. Light source 2310 and illuminator lens 2318 are positioned to properly concentrate light onto exterior cone surface 2301.

Figure 24:
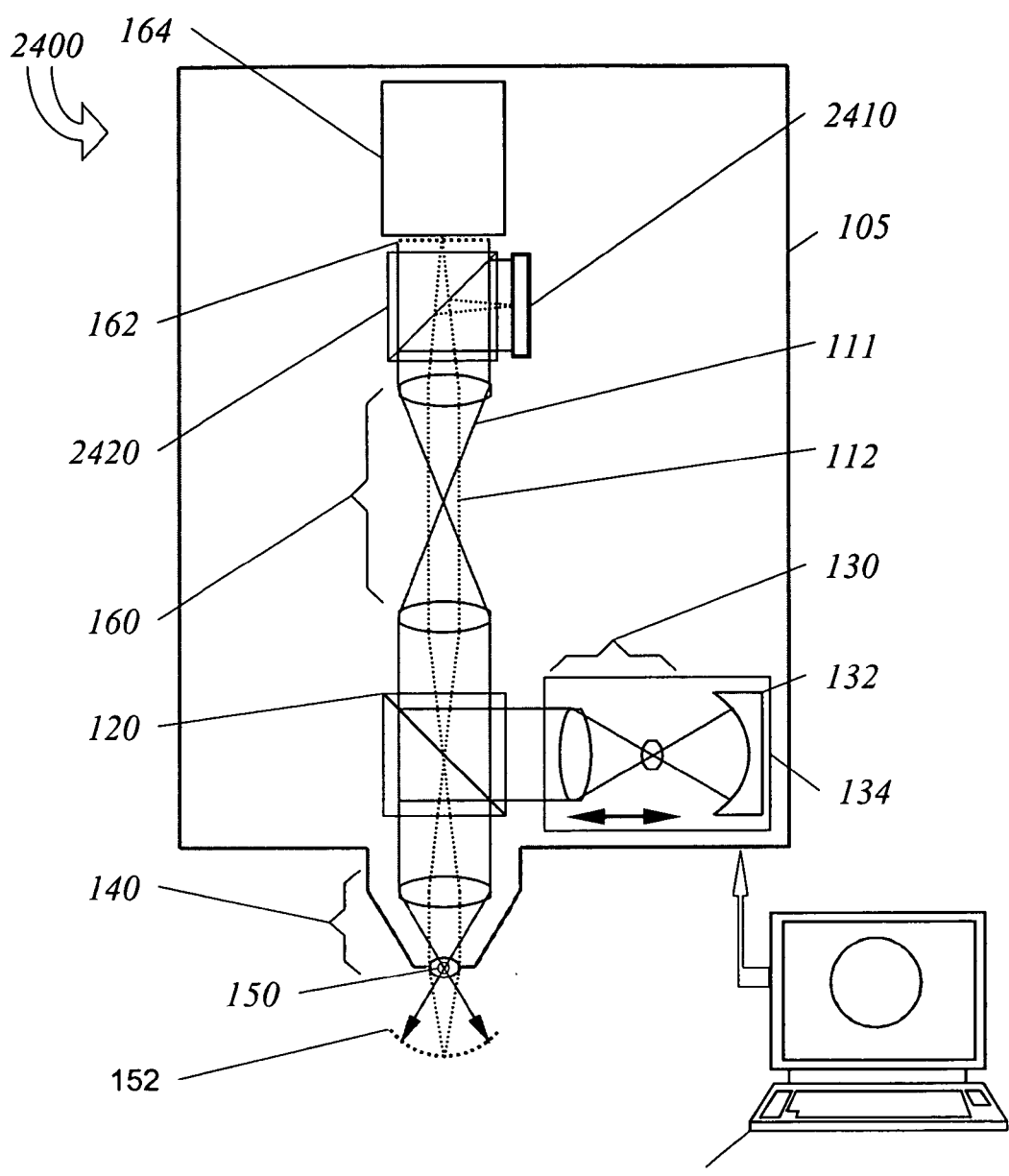
FIG. 24 is a schematic diagram of a sensor having an extended light source.

The aforementioned embodiments have an illumination source (e.g., a point source) that is imaged at infinity with respect to the camera. A different illumination layout is illustrated in FIG. 24, where the source 2410 is at least as large as the detector sensing area and is imaged onto the final image 162, instead of being imaged at the pupil of the imaging optics. Possible extended light sources are LED arrays, illuminated scattering screens, etc.

Any of the described embodiments can additionally include endoscopic optics for viewing down deep bores. Furthermore, chromatic dispersion correction optics in either the measurement or reference legs can improve fringe contrast, and simplify the optical design and data processing.

Although the embodiments described above are with respect to low coherence interferometry, other interferometry techniques can also be used. For example, interferometry methods using a long coherence length light source (e.g., lasers) can also be used. One such technique is phase shifting interferometry (PSI). In PSI, the phase of an detected interference signal is varied by, e.g., varying the wavelength of the light source or dithering the position of a reference surface. The difference in phase of the interference signal as a function of wavelength or reference surface position relates directly to the total optical path difference in the interferometer, which can itself be related to the distance of the surface to the datum point by measuring a calibration sphere of known radius of curvature. In PSI, interference images are acquired according to a phase-shifting algorithm so the each incremental change in interference signal can be related to a known wavelength change of, or OPD change between, reference and measurement wavefronts. Examples of PSI techniques can be found in U.S. Pat. No. 6,359,692, entitled "METHOD AND SYSTEM FOR PROFILING OBJECTS HAVING MULTIPLE REFLECTIVE SURFACES USING WAVELENGTH-TUNING PHASE-SHIFTING INTERFEROMETRY," to Peter de Groot, U.S. patent application Ser. No. 10/144,527, entitled "APPARATUS AND METHOD FOR PHASE-SHIFTING INTERFEROMETRY," to Michael Kuchel et al., and U.S. Provisional Application Ser. No. 60/339,214, entitled "FREQUENCY TRANSFORM PHASE-SHIFTING INTERFEROMETRY," to Leslie L. Deck.

Long wavelength (e.g., infrared, such as 0.75–10 µm) interferometry techniques can also be used in the aforementioned methods and systems. By using a longer source wavelength one can also establish a limited measurement volume where there is reduced distance uncertainty to the point datum, again by establishing this volume near a calibration sphere. In this case, a single-phase measurement may be sufficient. Moreover, surfaces that diffusely reflect visible wavelengths or light can appear specular to longer wavelengths. Hence, long wavelength sources can be used to characterize rough surfaces. Of course, for long wavelength interferometry, the system detector and optical components should be selected to perform appropriately at the light source wavelength. Long wavelength interferometry techniques are further described in U.S. Pat. No. 6,195,168, entitled "INFRARED SCANNING INTERFEROMETRY APPARATUS AND METHOD," to Xavier Colonna de Lega et al.

A number of embodiments of the invention have been described. Nevertheless, it will be understood that various modifications may be made without departing from the spirit and scope of the invention. For example, although described in the context of a conical valve surface, the invention also applies to other complex surface shapes, including, e.g., alternative valve seat geometries, countersunk holes and chamfers, non-conical but cylindrically shaped surfaces, and intersections of surfaces, such as a cylinder and a cone, or a sphere and a cone. Accordingly, other embodiments are within the scope of the following claims.

The invention claimed is:

1. Apparatus comprising:
   means for directing a measurement wavefront to reflect from a measurement surface and a reference wavefront to reflect from a reference surface, the measurement and reference wavefronts being derived from a common light source;
   means for directing the reflected measurement and reference wavefronts to overlap with one another and form an interference pattern, wherein paths for the measurement and reference wavefronts define an optical measurement surface corresponding to a theoretical test surface that would reflect the measurement wavefront to produce a constant optical path length difference between the measurement and reference wavefronts; and means for varying the radius of curvature of a locally spherical portion of the optical measurement surface to contact a conical portion of the measurement surface, and detecting the interference pattern as a function of the radius of curvature.

2. Apparatus comprising:

means for directing a measurement wavefront to reflect from a measurement surface and a reference wavefront to reflect from a reference surface, the measurement and reference wavefronts being derived from a common light source having a coherence length;

means for directing the reflected measurement and reference wavefronts to overlap with one another and form an interference pattern, wherein paths for the measurement and reference wavefronts define an optical measurement surface corresponding to a theoretical test surface that would reflect the measurement wavefront to produce a constant optical path length difference between the measurement and reference wavefronts; and means for varying the radius of curvature of a locally spherical portion of the optical measurement surface to contact the measurement surface, and detecting the interference pattern as a function of the radius of curvature, wherein the radius of curvature is varied over a distance greater than the coherence length of the light source.

3. The apparatus of claim 1 wherein the means for directing the measurement wavefront to reflect from the measurement surface and the reference wavefront to reflect from the reference surface comprises an interferometer.

4. The apparatus of claim 3 wherein the means for directing the reflected measurement and reference wavefronts to overlap with one another and form the interference pattern comprises the interferometer.

5. The apparatus of claim 3 wherein the interferometer is a Twyman-Green interferometer or a Fizeau interferometer.

6. The apparatus of claim 3 wherein the interferometer comprises measurement optics arranged to shape the measurement wavefront to include the locally spherical portion.

7. The apparatus of claim 6 wherein the measurement optics are positioned in the path of the measurement wavefront.

8. The apparatus of claim 6 wherein the measurement optics comprise an objective lens, which focuses the measurement wavefront toward a measurement point datum.

9. The apparatus of claim 6 further comprising reference optics configured to shape the reference wavefront prior to the reference surface.

10. The apparatus of claim 9 wherein the reference optics are positioned to direct the reference wavefront to the reference surface.

11. The apparatus of claim 9 wherein the reference optics comprise a reference lens that focuses the reference wavefront towards a reference focal point.

12. The apparatus of claim 9 wherein the means for varying the radius of curvature of the locally spherical portion of the optical measurement surface comprises a translation stage coupled to the interferometer and arranged to translate reference optics and reference surface to vary an optical path difference between the reflected measurement wavefronts and reflected reference wavefronts where they form the interference pattern.

13. The apparatus of claim 1 wherein the means for detecting the interference pattern as a function of the radius of curvature comprises a detector arranged to detect the interference pattern.

14. The apparatus of claim 13 further comprising an electronic processor in communication with the detector, the electronic processor being configured to determine a profile of the measurement surface based on the interference pattern detected by the detector as the translation stage translates the reference optics and reference surface.

15. The apparatus of claim 1 wherein the constant optical path length difference between the measurement and reference wavefronts is a zero optical path length difference.

16. The apparatus of claim 1 wherein the reference surface is a planar surface.

17. The apparatus of claim 1 wherein the reference surface is a curved surface.

18. The apparatus of claim 1 further comprising an object mount for positioning the measurement surface relative to the means for directing the measurement wavefront to reflect from the measurement surface and the reference wavefront to reflect from the reference surface.

19. The apparatus of claim 18 wherein the object mount positions an object having a conical measurement surface relative to the means for directing the measurement wavefront to reflect from the measurement surface and the reference wavefront to reflect from the reference surface.

20. The apparatus of claim 1 wherein the means for directing the measurement wavefront to reflect from the measurement surface and the reference wavefront to reflect from the reference surface comprises imaging optics which image a portion of the measurement surface to an image plane.

21. The apparatus of claim 20 wherein the imaging optics also image the reference surface to the image plane.

22. The apparatus of claim 20 wherein the detecting means is positioned at the image plane.

23. The apparatus of claim 1 wherein the common light source has a coherence length and the radius-varying means is arranged to vary the radius of curvature of the locally spherical portion of the optical measurement surface over a distance greater than the coherence length of the light source.

24. The apparatus of claim 2, wherein the measurement surface includes a conical surface.

25. The apparatus of claim 2, wherein the means for directing the reflected measurement and reference wavefronts to overlap with one another is an interferometer.

26. The apparatus of claim 25, wherein the interferometer is a Twyman-Green interferometer or a Fizeau interferometer.

27. The apparatus of claim 25, further comprising a means for focusing the reference wavefront towards a reference focal point.

28. The apparatus of claim 27, wherein the means for focusing the reference wavefront comprises reference optics.

29. The apparatus of claim 28, wherein the means for varying the radius of curvature of the locally spherical portion of the optical measurement surface is a translation stage coupled to the interferometer and configured translate the reference optics relative to the interferometer.

* * * * *